United States Patent
Chabot et al.

(10) Patent No.: US 9,783,547 B2
(45) Date of Patent: Oct. 10, 2017

(54) WATER SOLUBLE 4-AZAPODOPHYLLOTOXIN ANALOGS

(71) Applicants: CENTRE NATIONAL DE LA RECHERCHE SCIENTIFIQUE (CNRS), Paris (FR); UNIVERSITE PARIS DESCARTES, Paris (FR); INSTITUT NATIONAL DE LA SANTE ET DE LA RECHERCHE MEDICALE (INSERM), Paris (FR); ECOLE NATIONALE SUPERIEURE DE CHIMIE DE PARIS, Paris (FR)

(72) Inventors: Guy Chabot, Charenton le Pont (FR); Sylviane Giorgi-Renault, Paris (FR); Stéphanie Desbene-Finck, Paris (FR); Philippe Helissey, Villeparisis (FR); Raphaël Labruere, Orsay (FR); Marlène Testud, Paris (FR); Daniel Scherman, Paris (FR)

(73) Assignees: CENTRE NATIONAL DE LA RECHERCHE SCIENTIFIQUE (CNRS), Paris (FR); UNIVERSITE PARIS DESCARTES, Paris (FR); INSTITUT NATIONAL DE LA SANTE ET DE LA RECHERCHE MEDICALE (INSERM), Paris (FR); ECOLE NATIONALE SUPERIEURE DE CHIMIE DE PARIS, Paris (FR)

( * ) Notice: Subject to any disclaimer, the term of this patent is extended or adjusted under 35 U.S.C. 154(b) by 0 days.

(21) Appl. No.: 15/111,711

(22) PCT Filed: Jan. 15, 2015

(86) PCT No.: PCT/EP2015/050702
§ 371 (c)(1),
(2) Date: Jul. 14, 2016

(87) PCT Pub. No.: WO2015/107119
PCT Pub. Date: Jul. 23, 2015

(65) Prior Publication Data
US 2016/0333022 A1    Nov. 17, 2016

(30) Foreign Application Priority Data
Jan. 15, 2014    (EP) ..................... 14305056

(51) Int. Cl.
*C07D 219/10* (2006.01)
*C07D 491/056* (2006.01)
(Continued)

(52) U.S. Cl.
CPC ........ *C07D 491/056* (2013.01); *A61K 31/473* (2013.01); *A61K 31/4741* (2013.01);
(Continued)

(58) Field of Classification Search
CPC .............. A61K 31/473; A61K 31/4741; A61K 31/513; A61K 31/519; A61K 31/675;
(Continued)

(56) References Cited

U.S. PATENT DOCUMENTS

| 4,814,470 A | 3/1989 | Colin et al. |
| 5,620,985 A | 4/1997 | Jacquesy et al. |

(Continued)

FOREIGN PATENT DOCUMENTS

| EP | 0253738 A1 | 1/1988 | |
| EP | 0179383 B1 * | 5/1991 | .......... C07C 255/00 |

(Continued)

OTHER PUBLICATIONS

Aknin et al., "A new synthetic approach to functionalize pyrimido[4,5-b]quinoline-2,4(1H,3H)-diones via a three-component one-pot reaction," Mol Divers, vol. 14, 2010 (Published online May 19, 2009), pp. 123-130.
Bane et al., "High-Throughput Screening of Microtubule-Interacting Drugs," Methods in Molecular Medicine, Microtubule Protocols, vol. 137, 2007, pp. 281-288.
Barron et al., "A fluorescence-based high-throughput assay for antimicrotubule drugs," Analytical Biochemistry, vol. 315, 2003, pp. 49-56.
Bonne et al., "4',6-Diamidino-2-phenylindole, a Fluorescent Probe for Tubulin and Microtubules," The Journal of Biological Chemistry, vol. 260, No. 5, Mar. 10, 1985, pp. 2819-2825.
Bouïs et al., "Endothelium in vitro: A review of human vascular endothelial cell lines for blood vessel-related research," Angiogenesis, vol. 4, 2001, pp. 91-102.
Corbett et al., "Evaluation of Single Agents and Combinations of Chemotherapeutic Agents in Mouse Colon Carcinomas," Cancer, Supplement, vol. 40, No. 5, Nov. 1977, pp. 2660-2680.
Corbett et al., "Toxicity and Anticancer Activity of a New Triazine Antifolate (NSC 127755)," Cancer Research, vol. 42, May 1982, pp. 1707-1715.

(Continued)

*Primary Examiner* — Sarah Pihonak
(74) *Attorney, Agent, or Firm* — Birch, Stewart, Kolasch & Birch, LLP

(57) ABSTRACT

The present invention relates to 4-azapodophyllotoxin analogs of formula (I) in which X, $R_1$, $R_2$, $R_3$, $R_4$ and Ar are as defined in claim 1, preferably a pharmaceutically acceptable salt thereof, optionally in the form of a solvate, a composition comprising said analogs, their use as medicament, in particular for the treatment of cancer, and a process for their preparation.

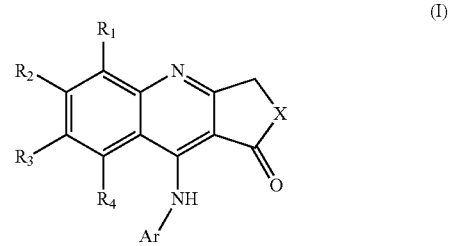

18 Claims, 5 Drawing Sheets

(51) Int. Cl.
A61K 31/473 (2006.01)
A61K 31/4741 (2006.01)
A61K 31/513 (2006.01)
A61K 31/519 (2006.01)
A61K 31/675 (2006.01)
A61K 31/704 (2006.01)
A61K 33/24 (2006.01)
A61K 45/06 (2006.01)

(52) U.S. Cl.
CPC .......... *A61K 31/513* (2013.01); *A61K 31/519* (2013.01); *A61K 31/675* (2013.01); *A61K 31/704* (2013.01); *A61K 33/24* (2013.01); *A61K 45/06* (2013.01); *C07D 219/10* (2013.01)

(58) Field of Classification Search
CPC ...... A61K 31/704; A61K 33/24; A61K 45/06; C07D 219/10; C07D 491/056
See application file for complete search history.

(56) References Cited

U.S. PATENT DOCUMENTS

| | | | |
|---|---|---|---|
| 5,622,964 | A | 4/1997 | Ohnmacht, Jr. et al. |
| 6,548,515 | B1 | 4/2003 | Husson et al. |
| 2004/0180917 | A1 | 9/2004 | Husson et al. |
| 2004/0198981 | A1 | 10/2004 | Husson et al. |
| 2007/0253957 | A1 | 11/2007 | Zhang et al. |

FOREIGN PATENT DOCUMENTS

| | | | |
|---|---|---|---|
| EP | 0179383 | B1 | 5/1991 |
| EP | 1103554 | A1 | 5/2001 |
| WO | WO 95/03312 | A1 | 2/1995 |
| WO | WO 02/094835 | A1 | 11/2002 |
| WO | WO 02/094840 | A2 | 11/2002 |
| WO | WO 2006/041900 | A2 | 4/2006 |
| WO | WO 2013/024282 | A2 | 2/2013 |

OTHER PUBLICATIONS

Corbett et al., "Tumor Induction Relationships in Development of Transplantable Cancers of the Colon in Mice for Chemotherapy Assays, with a Note on Carcinogen Structure," Cancer Research, vol. 35, Sep. 1975, pp. 2434-2439.
Desbène et al., "Drugs that Inhibit Tubulin Polymerization: The Particular Case of Podophyllotoxin and Analogues," Curr. Med. Chem.—Anti-Cancer Agents, vol. 2, No. 1, 2002, pp. 1-20.
Edgell et al., "Permanent cell line expressing human factor VIII-related antigen established by hybridization," Proc. Natl. Acad. Sci. USA, Cell Biology, vol. 80, Issue 12, Jun. 1983, pp. 3734-3737.
Giorgi-Renault, "Communication 4-aza-2,3-didéhydropodophyllotoxines: nouveaux lignanes à activity antitumorale obtenus par une synthèse en une seule étape," Ann Pharm Fr, vol. 63, 2005, pp. 63-68, with an English abstract.
Gutsulyak et al., "Reaction of Secondary Aromatic Amines with Formaldehyde and Cyclic β-Diketones," Zhurnal Organicheskoi Khimii (Journal of Organic Chemistry of the USSR), vol. 16, No. 9, Sep. 1980 (Original article submitted Apr. 24, 1979), pp. 1592-1598, XP009177911.
Hitotsuyanagi et al., "4-Aza-2,3-dehydro-4-deoxypodophyllotoxins: Simple Aza-podophyllotoxin Analogues Possessing Potent Cytotoxicity," Bioorganic & Medicinal Chemistry Letters, vol. 10, No. 4, 2000, pp. 315-317.
Hitotsuyanagi et al., "A Facile Synthesis of the 4-Aza-analogs of 1-Arylnaphthalene Lignans Chinensin, Justicidin B, and Taiwanin C," Tetrahedron Letters, vol. 38, No. 48, 1997, pp. 8295-8296.
International Search Report (Form PCT/ISA/210) for International Application No. PCT/EP2015/050702, dated Mar. 31, 2015.
Labruère et al., "Design and Effective Synthesis of the First 4-Aza-2,3-didehydropodophyllotoxin Rigid Aminologue: A N-Methyl-4-[(3,4,5-trimethoxyphenyl)amino)]-1,2-dihydroquinoline-lactone," J. Org. Chem., vol. 73, No. 9, 2008 (Published on Web Apr. 2, 2008), pp. 3642-3645.
Labruère et al., "Design, Synthesis, and Biological Evaluation of the First Podophyllotoxin Analogues as Potential Vascular-Disrupting Agents," ChemMedChem, vol. 5, No. 12, 2010, pp. 2016-2025.
Lv et al., "Recent Advances in Semisynthesis, Biosynthesis, Biological Activities, Mode of Action, and Structure-Activity Relationship of Podophyllotoxins: An Update (2008-2010)," Mini-Reviews in Medicinal Chemistry, vol. 11, No. 10, 2011, pp. 901-909.
Mayo, "Biologic Characterization of the Subcutaneously Implanted Lewis Lung Tumor," Cancer Chemotherapy Reports Part 2, vol. 3, No. 1, Nov. 1972 (Presented at the Screening Contractors Meeting, Apr. 14, 1972), pp, 325-330.
Oppegard et al., "Novel acridine-based compounds that exhibit an anti-pancreatic cancer activity are catalytic inhibitors of human topoisomerase II," European Journal of Pharmacology, vol. 602, 2009 (Available online Dec. 3, 2008), pp. 223-229.
Schabel et al., "Quantitative Evaluation of Anticancer Agent Activity in Experimental Animals," Pharmac Ther. A, vol. 1, No. 4-E, 1977, pp. 411-435.
Scudiero et al., "Evaluation of a Soluble Tetrazolium/Formazan Assay for Cell Growth and Drug Sensitivity in Culture Using Human and Other Tumor Cell Lines," Cancer Research, vol. 48, Sep. 1, 1988, pp. 4827-4833.
Shutske et al., "9-Amino-1,2,3,4-tetrahydroacridin-1-ols: Synthesis and Evaluation as Potential Alzheimer's Disease Therapeutics," J. Med. Chem., vol. 32, No. 8, 1989, pp. 1805-1813, XP000867003.
Tratrat et al., "A Multicomponent Reaction for the One-Pot Synthesis of 4-Aza-2,3-didehydropodophyllotoxin and Derivatives," Organic Letters, vol. 4, No. 19, 2002 (Published on Web Aug. 23, 2002), pp. 3187-3189.
You, "Podophyllotoxin Derivatives: Current Synthetic Approaches for New Anticancer Agents," Current Pharmaceutical Design, vol. 11, No. 13, 2005, pp. 1695-1717.

* cited by examiner

WATER SOLUBLE 4-AZAPODOPHYLLOTOXIN ANALOGS

The present invention relates to 4-azapodophyllotoxin analogs, a composition comprising said analogs, their use as medicament, in particular for the treatment of cancer, and a process for their preparation.

Podophyllotoxin is a natural lignan extracted from the roots and rhizomes of the plant *Podophyllum peltatum* and *Podophyllum emodi*. This plant toxin inhibits the assembly of microtubules and is toxic to mammalian cells, including cancer cells. However, attempts to use podophyllotoxin in the treatment of human cancers have been unsuccessful because of serious side effects such as nausea, vomiting, diarrhea, severe gastro-intestinal toxicity, and damage to normal tissues.

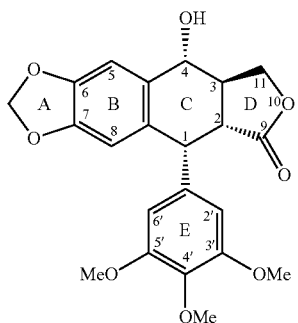

Podophyllotoxin structure and usual numbering

The structural features of podophyllotoxin include a polycyclic moiety (fused rings ABCD) comprising a five-membered lactone (ring D), one aromatic ring (ring B), and a ring bearing a hydroxyl (ring C) and an aryl (ring E) substituent. Of note, podophyllotoxin contains 4 chiral centers.

Extensive structure modifications of podophyllotoxin have been performed in order to obtain more potent and less toxic anticancer agents, which have led by hemisynthesis to epipodophyllotoxins, including two clinically active drugs, i.e., etoposide (VP16) and teniposide (VM26). Both etoposide and teniposide include a sugar moiety on the hydroxyl substituent of ring C, which improves the water solubility of said compounds, thus facilitating their formulation as drugs. Of note, a prodrug of etoposide—a phosphate derivative—was also developed (Etopophos). The phosphate group greatly contributes to the improvement of water solubility of the drug.

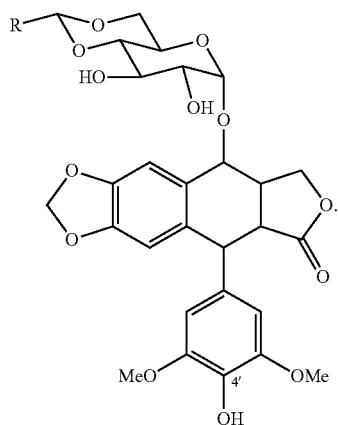

Teniposide, etoposide and its phosphate prodrug (etopophos)

Teniposide (VM26) R =

Etoposide (VP16) R = CH$_3$

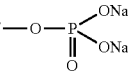

Etopophos

Etoposide, teniposide and Etopophos are indicated in the treatment of several tumors such as small-cell lung cancer, testicular carcinoma, leukemia, and lymphoma. The mechanism of action of etoposide and teniposide are entirely different from that of the parent compound podophyllotoxin, because they act as topoisomerase II inhibitors and do not inhibit tubulin polymerization (for reviews, see Desbène and Giorgi-Renault, 2002. Drugs that inhibit tubulin polymerization: the particular case of podophyllotoxin and analogues. Curr. Med. Chem. Anticancer Agents, 2, 71-90; Lv, M., Mini-Reviews in Medicinal Chemistry 2011, 11, 901-909; You, Y., Curr Pharm Des, 2005, 11, 1695-1717).

Other podophyllotoxin analogs in which ring C contains a nitrogen atom (4-aza-2,3-didehydropodophyllotoxins) have been described in the prior art (see in particular EP 1 103 554; WO02/094835; WO02/094840; Tratrat et al Organic Letters 2002, 4, 3187-3189). From a chemical point of view, the 4-aza-2,3-didehydro analogues present the advantages of possessing only one chiral center and a stable unsaturated lactone ring. These antitumoral molecules are tubulin polymerization inhibitors and are very cytotoxic to cancer cells in vitro. The described 4-aza-2,3-didehydropodophyllotoxins did not exhibit satisfactory water solubility, a parameter of great importance when it comes to formulation, in particular for administration to humans via oral or intravenous route. Indeed, it is highly desirable to obtain analogs with reasonable water solubility, in order to ease formulation and to improve bioavailability.

Several derivatives which were found to exhibit lower cytotoxicity associated with high tubulin inhibiting activity appear as good vascular disrupting agent (VDA) candidates. Indeed, tumour growth and metastasis are dependent on tumour-associated blood vessels formation. VDAs are a new class of anticancer drugs that selectively destroy tumour vasculature. In particular, they target the cytoskeleton of endothelial cells, therefore blocking cancer cells proliferation and metastatic dissemination through the vasculature. To date, currently developed small molecular weight VDAs are mostly constituted by tubulin-binding agents. Most VDAs are actually based on natural compound original leads. Some compounds are currently undergoing preclinical or clinical evaluation, however, their affinity for normal endothelial cells and the clinical toxicities observed severely hamper their development. Therefore, it is of interest to design new VDAs based on these natural compound leads in order to improve their efficacy and decrease their systemic toxicities.

In the azapodophyllotoxin series, a first analog with a 4-aza-1,2-didehydropodophyllotoxin skeleton has been described (Labruère et al 2010 Chem. Med. Chem. 2010, 5, 2016-2025; J. Org. Chem. 2008, 73, 3642-3645) but it did not present interesting in vivo activity. There is thus a need for effective azapodophyllotoxin analogs antitumor agents, which are water soluble, less toxic to normal cells and that are cytotoxic to cancer cells and also destroy tumor vasculature.

The Applicants have found new water soluble aromatic azapodophyllotoxin (4-aza-1,2,3,4-tetradehydropodophyllotoxin, i.e. a 4-arylaminoquinoline nucleus annelated to a cycloketone) analogs exhibiting antitumor properties, which act as antivascular or vascular disruptive agents through tubulin polymerization inhibition. These drugs target neovasculature in tumors, in particular the cytoskeleton of endothelial cells, thereby blocking cancer cells proliferation and metastatic dissemination through the vasculature.

The present invention thus relates to said aromatic azapodophyllotoxin (4-aza-1,2,3,4-tetradehydropodophyllotoxin) analogs, preferably in salified form, which also exhibit improved water solubility, and are useful as antivascular agents, in particular for the treatment of cancer.

The present invention thus relates, in a first aspect, to a compound of formula (I):

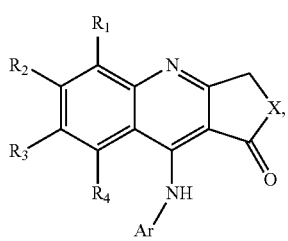

in which $R_1$, $R_2$, $R_3$, $R_4$, X and Ar are as described below, preferably a pharmaceutically acceptable salt thereof, optionally in the form of a solvate thereof.

In another aspect, the present invention relates to a composition comprising said compounds of formula (I), preferably a pharmaceutically acceptable salt thereof, and a pharmaceutically acceptable excipient.

In another aspect, the present invention relates to a kit comprising at least:
- a first composition comprising said compounds of formula (I), preferably a pharmaceutically acceptable salt thereof, and a pharmaceutically acceptable excipient, and
- a second composition comprising another antitumoral agent, for simultaneous, staggered or sequential use.

In another aspect, the present invention relates to the compounds of formula (I), preferably a pharmaceutically acceptable salt thereof, or the composition or the kit of the invention, for their use as medicament, in particular as cytotoxic agent, or antivascular agent, advantageously in the treatment of cancer.

In another aspect, the present invention relates to a combination therapy comprising administering to a patient in need thereof a composition of the invention, for simultaneous, staggered or sequential use with a treatment by radiotherapy surgery, hyperthermia, or in combination with another anticancer drug.

In another aspect, the present invention relates to a method of preparing the compounds of the invention.

Figure 1:
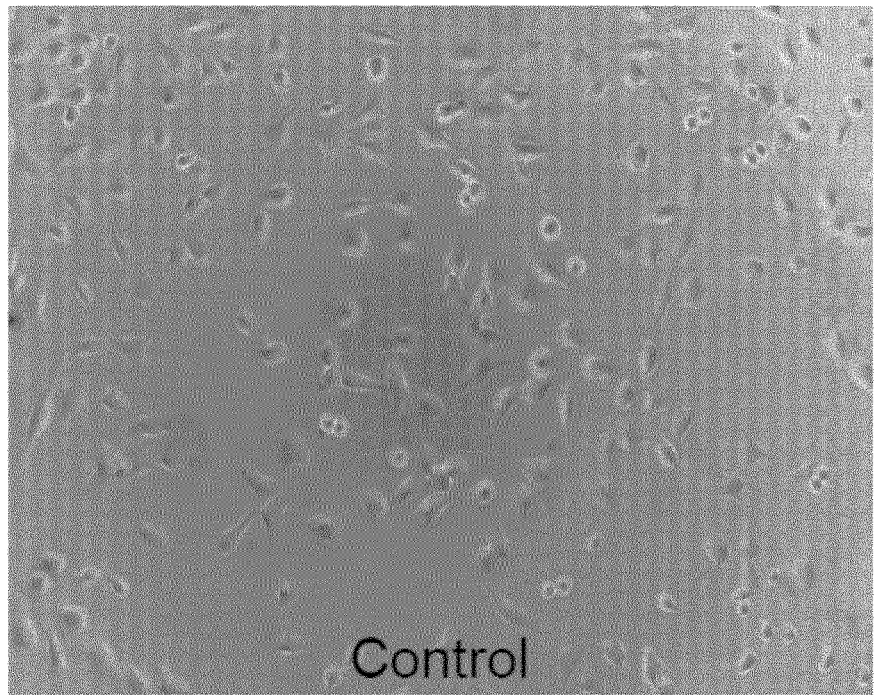
FIG. 1. Typical rounding up of endothelial cells exposed to SGR307 hydrochloride (SGR307.HCl) (see structure below) for a short 2 hour time period at a concentration of 1 μM, versus control (rounding up of endothelial cells exposed to the excipient (1% DMSO in the cell culture medium) for a short 2 hour time period at a concentration of 1 μM).
Figure 1:
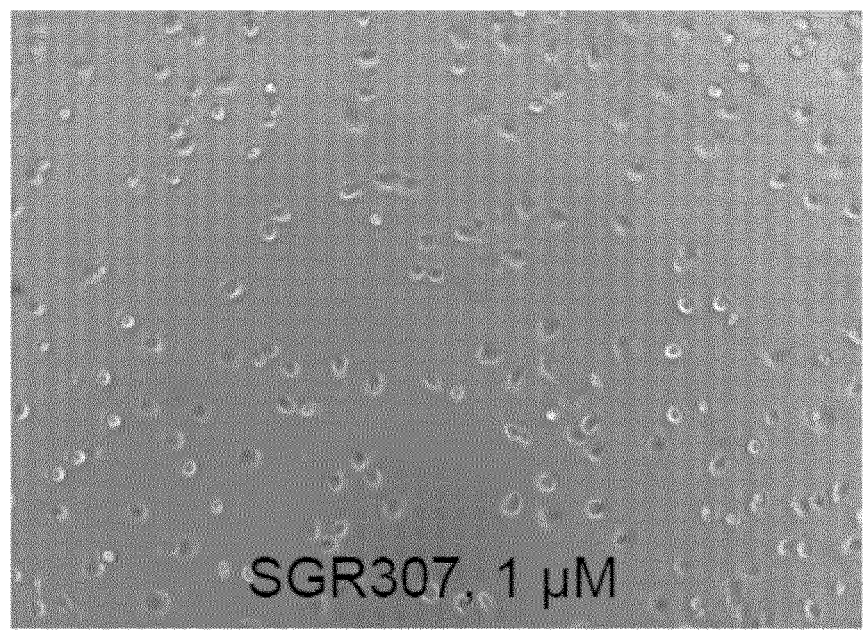

The present invention concerns a compound of formula (I):

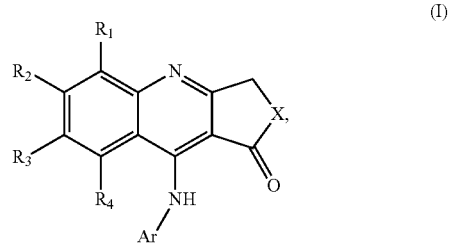

in which

X represents —CH$_2$— or —CH$_2$CH$_2$—;

$R^1$ and $R^4$ are independently selected from the group consisting of H, halogen, $C_1$-$C_4$-alkyl;

$R^2$ and $R^3$ are independently selected from the group consisting of H, OH, $C_1$-$C_4$ alkyl, $C_1$-$C_4$-alkoxy, $C_1$-$C_4$-alkylthio, halogen, trifluoromethyl, CN;

or $R^2$ and $R^3$, taken together, form a bridging group selected from the group consisting of —(CH$_2$)$_n$— and —O—(CH$_2$)$_m$—O—, n being an integer between 3 and 4 and m being 1 or 2;

Ar represents a phenyl or naphthyl group optionally substituted with one to four substituents independently selected from the group consisting of $C_1$-$C_4$-alkyl, OH, $C_1$-$C_4$-alkoxy, $C_1$-$C_4$-alkylthio, halogen, trifluoromethyl, CN;

or preferably a pharmaceutically acceptable salt thereof, optionally in the form of a solvate thereof.

In a particular embodiment, Ar represents a phenyl substituted on position 2 or 4 (ortho or para position) by at least one $C_1$-$C_4$-alkoxy substituent or a naphthyl group substituted by at least one substituents $C_1$-$C_4$-alkoxy, and the phenyl or naphthyl group is further optionally substituted with one to three more substituents independently selected from the group consisting of $C_1$-$C_4$-alkyl, OH, $C_1$-$C_4$-alkoxy, $C_1$-$C_4$-alkylthio, halogen, trifluoromethyl, CN. Advantageously, in this embodiment, Ar represents a phenyl group substituted on position 2 or 4 by at least one substituents $C_1$-$C_4$-alkoxy, and optionally substituted with one to three more substituents independently selected from the group consisting of $C_1$-$C_4$-alkyl, OH, $C_1$-$C_4$-alkoxy, $C_1$-$C_4$-alkylthio, halogen, trifluoromethyl, CN.

In a preferred embodiment, Ar represents a phenyl or naphthyl group (preferably a phenyl group) substituted by two substituents independently selected from the group consisting of OH and $C_1$-$C_4$-alkoxy, and optionally substituted with one to two more substituents independently selected from the group consisting of $C_1$-$C_4$-alkyl, OH, $C_1$-$C_4$-alkoxy, $C_1$-$C_4$-alkylthio, halogen, trifluoromethyl, CN. More preferably, Ar represents a phenyl or naphthyl group substituted by three substituents independently selected from the group consisting of OH and $C_1$-$C_4$-alkoxy, and even more preferably Ar represents a phenyl or naphthyl group substituted by three $C_1$-$C_4$-alkoxy groups.

Pharmaceutically acceptable salts include those derived from pharmaceutically acceptable inorganic and organic acids. Examples of suitable acids include hydrochloric, hydrobromic, sulfuric, nitric, perchloric, boric, ascorbic, fumaric, maleic, phosphoric, glycolic, lactic, salicylic, succinic, hemisuccinic, toluene-p-sulfuric, tartaric, acetic, citric, methanesulfonic, formic, benzoic, malonic, hexanoic, hippuric, heptanoic, hydroxyethanesulfonic, phenylglycoxylic, nicotinic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Preferred pharmaceutically acceptable salts include hydrochloride, lactate, 2-hydroxyethanesulfonate, and methanesulfonate salts.

Solvates are chemical complexes formed by the interaction of a solvent and a solute, here the compound of formula (I) or salt thereof. Preferred pharmaceutically acceptable solvates are hydrates, and solvates of alcoholic solvents, such as ethanol. Preferably, the solvate is a hydrate and/or an alcoholate, more preferably a hydrate.

Within the framework of the present invention, the expression "$C_1$-$C_4$-alkyl" is understood as a hydrocarbon chain comprising from 1 to 4 carbon atoms (C1-C4), linear or branched. Examples of alkyl radicals comprising from 1 to 4 carbon atoms include methyl, ethyl, propyl, butyl, isopropyl, and isobutyl radicals.

Within the framework of the present invention, the expression "$C_1$-$C_4$-alkoxy" is understood as an alkoxy chain comprising from 1 to 4 carbon atoms (C1-C4), that is to say a $C_1$-$C_4$ alkyl linked to an oxygen atom, which in turn is linked to the rest of the molecule.

The term "halogen" used herein designates chlorine, bromine, iodine or fluorine, preferably chlorine or fluorine.

Preferably, $R^1$ and $R^4$ are independently selected from the group consisting of H, halogen, and methyl, even more preferably at least one of $R^1$ and $R^4$ is hydrogen. In a preferred embodiment, $R^1$ and $R^4$ both represent H.

Advantageously, $R^2$ and $R^3$ are independently selected from the group consisting of H, OH, $C_1$-$C_4$ alkyl, $C_1$-$C_4$-alkoxy, or $R^2$ and $R^3$, taken together, form a bridging group selected from the group consisting of —$(CH_2)_n$— and —O—$(CH_2)_m$—O—, n being an integer between 3 and 4 and m being 1 or 2. More advantageously, $R^2$ and $R^3$ are independently selected from the group consisting of OH, $C_1$-$C_4$ alkyl, $C_1$-$C_4$-alkoxy, or $R^2$ and $R^3$, taken together, form a bridging group selected from the group consisting of —$(CH_2)_n$— and —O—$(CH_2)_m$—O—, n being an integer between 3 and 6, preferably 3 or 4, and m being 1 or 2.

Preferably, Ar represents a phenyl group substituted with one to three substituents independently selected from the group consisting of $C_1$-$C_4$-alkyl, $C_1$-$C_4$-alkoxy, OH groups, more preferably two or three $C_1$-$C_4$-alkoxy groups, and even more preferably, Ar is a 3,4,5-trimethoxyphenyl group.

In an advantageous embodiment, X represents —$CH_2CH_2$— and both $R^1$ and $R^4$ both represent H.

In another embodiment, $R^2$ and $R^3$, taken together, form the bridging group —O—$(CH_2)_m$—O— with m being 1 or 2, and both $R^1$ and $R^4$ both represent H. In this embodiment, the compound of the invention is best described by formula (Ia):

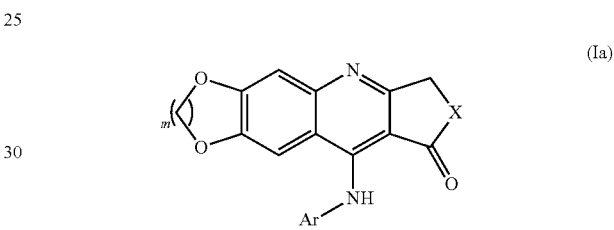

wherein X and Ar are as described above and m is 1 or 2.

In a preferred embodiment, the present invention relates to a compound of formula (Ib):

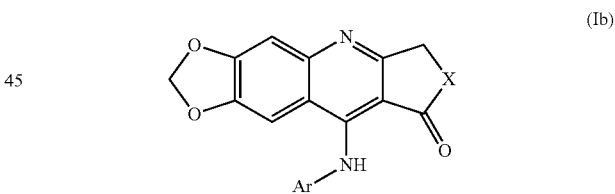

wherein X and Ar are as described above.

In a further preferred embodiment, the present invention relates to a compound of formula (Ic):

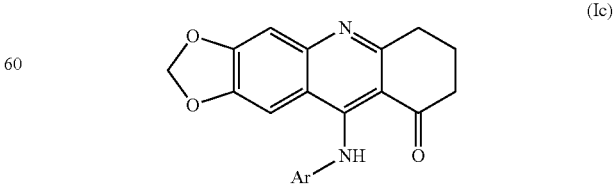

wherein Ar is as described above.

In particular, the compound of the invention is:
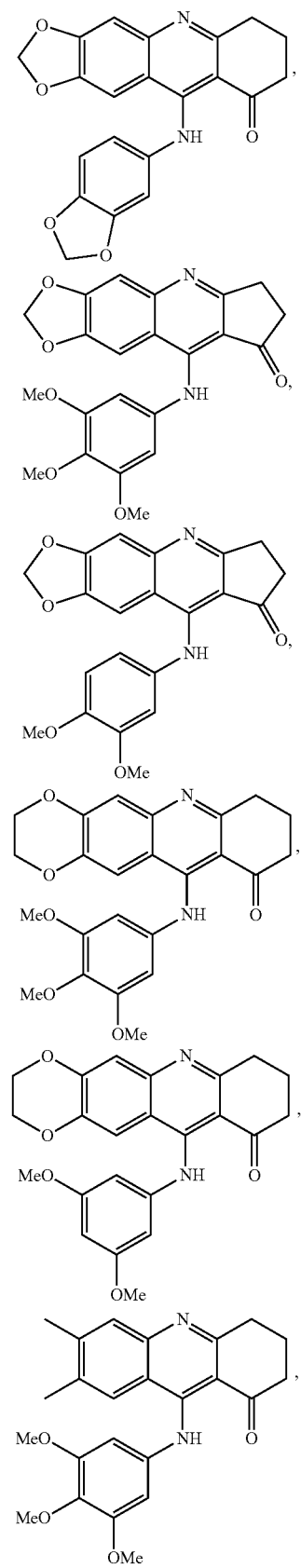
preferably
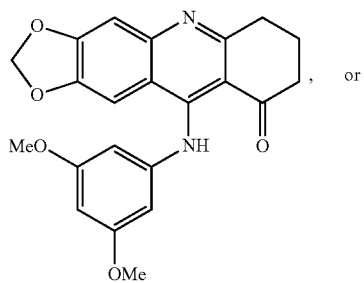

-continued

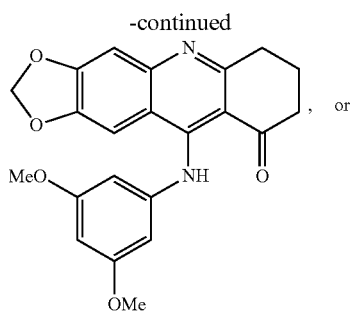

, or

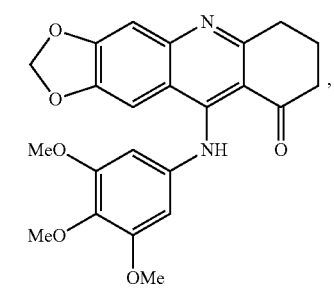 [SMILES: COc1cc(Nc2c3c(nc4cc5c(cc24)OCO5)CCCC3=O)cc(OC)c1OC]

, more preferably

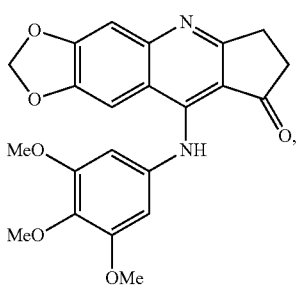

,

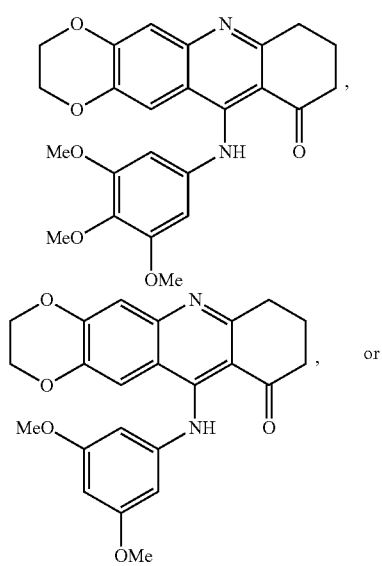

, or

-continued

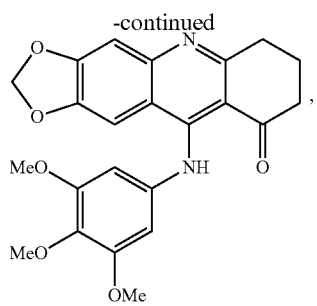

, or salt thereof, preferably a hydrochloride, lactate, 2-hydroxyethanesulfonate, and methanesulfonate salt thereof, and most preferably a hydrochloride salt thereof, optionally in the form of a solvate thereof.

Preferably, the compound of the invention is:

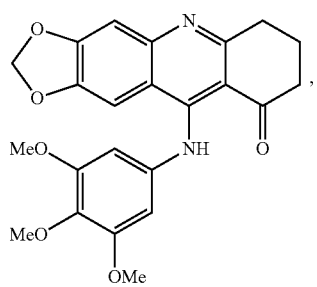

, also called SGR307, or salt thereof, preferably a hydrochloride, lactate, 2-hydroxyethanesulfonate, and methanesulfonate salt thereof, and most preferably a hydrochloride salt thereof.

The compounds contemplated in the present invention are only those which are 'chemically stable' as will be appreciated by those skilled in the art.

The invention includes pharmaceutically acceptable derivatives of compounds of formula (I). A "pharmaceutically acceptable derivative" refers to any pharmaceutically acceptable salt, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being produced enzymatically or chemically. This includes, for example, hydroxylated or oxidized derivative compounds, or conjugates thereof, of the invention.

In addition, within the scope of the invention is the use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula (I) may be made using the general synthetic methods described below, which also constitute part of the invention.

In another aspect, the present invention relates to a composition comprising as active ingredient at least one compound of formula (I), preferably a pharmaceutically acceptable salt thereof, optionally in the form of a solvate, and a pharmaceutically acceptable excipient.

The inventive pharmaceutical compositions can be, for example, compositions administered by oral, or parenteral route, preferably parenteral, in particular intravenous route.

A first preferred route of administration is the oral route. Examples of compositions administered by oral route include tablets, gelatin capsules, granules, microspheres, nanoemulsions, liposomes, powders and oral solutions or suspensions.

Another preferred route of administration is the parenteral, for instance intravenous route. Indeed, the compounds of the invention are soluble in aqueous solutions, advantageously they exhibit solubility in water greater than 5 g/L, preferably greater than 10 g/L. For instance, the compounds of the invention have a solubility of between 5 and 10 g/L. For instance, the compounds of the invention, preferably as salts, may be formulated in aqueous solutions such as mixtures of dextrose 5% in water, alcohol/polysorbate/water solvents, notably ethanol/Tween®/water and mannitol/water or with the assistance of cyclodextrins suitable for administration in human, which are frequently used for administration by intravenous route. The compounds of the invention, preferably as salts, may also be formulated as nanoemulsions or liposomes. The compositions according to the invention can thus be administered by intravenous route. Therefore, in a particular embodiment, the composition of the invention is formulated as an injectable solution.

The compositions of the invention typically contain between 0.01% and 10% by weight, preferably between 0.1% and 5% by weight of said compound of formula (I), relative to the total weight of the composition.

The inventive composition may further contain another active substance.

In another aspect, the present invention relates to a kit comprising at least:
 a first composition comprising said compound of formula (I), and a pharmaceutically acceptable excipient, and
 a second composition comprising another antitumoral agent, such as cisplatine methotrexate, cyclophosphamide, doxorubicin, fluorouracil for instance,
for simultaneous, staggered or sequential use.

The one skilled in the art will of course select the second composition comprising another antitumoral agent taking into account the nature and stage of the tumor or cancer to be treated, as well as the age, sex, weight and sensitivity of the patient to be treated.

In one embodiment, the compounds or compositions or kit of the present invention may be used alone or in combination, simultaneously, separately or sequentially, with ionizing or non-ionizing radiations or hyperthermia.

In another aspect, the present invention relates to the compounds of formula (I), the composition or the kit of the invention, for use as medicament, in particular as cytotoxic agent, antivascular agent or in the treatment of cancer.

Notably, the compounds of formula (I), the composition or the kit of the invention, may be used for treating cancer, in particular selected from the group consisting of melanoma, lung carcinoma, colon carcinoma, colorectal cancer, breast cancer, brain tumors, pancreas cancer, leukemia, prostate cancer, lymphoma, liver cancer, ovarian cancer, preferably melanoma, lung carcinoma, colorectal carcinoma breast cancer, ovarian carcinoma and colon carcinoma, more preferably selected from the group consisting of ovarian cancer, melanoma, lung carcinoma, and colon carcinoma.

In a particular embodiment, the cancer is a multi-drug resistant cancer. For instance, said cancer may be cisplatin-resistant.

The present invention, according to another aspects, also relates to a method of treating the above disorders which comprises administering to a patient in need thereof, an effective dose of a compound according to the invention, or a pharmaceutically acceptable salt thereof or a composition according to the invention, preferably by the parenteral, in particular intravenous, or oral route. The effective dose of a compound of the invention depends on many parameters such as, for example, the chosen route of administration, weight, age, sex, status of the pathology treated and the sensitivity of the individual to be treated.

In another aspect, the present invention relates to a combination therapy comprising administering to a patient in need thereof a composition of the invention, for simultaneous, staggered or sequential use with a treatment by radiotherapy, surgery, or hyperthermia.

According to another aspect, the present invention relates to the use of the compounds of formula (I) or the composition of the invention for the manufacture of a medicament, in particular a as cytotoxic agent, antivascular agent, preferably for treating cancer, in particular the above disorders.

The compounds of formula (I) induce rounding-up of endothelial cells and destruction of endothelial cords in vitro at nanomolar concentrations. The inventive compounds of formula (I) also inhibit tubulin polymerization. They are cytotoxic at micromolar concentrations on murine and human cancer cells, with a level of activity comparable to combretastatin A4 (CA4). They are also active on multidrug-resistant (MDR) human cancer cells, in particular on a cisplatin-resistant human cancer cell line. The inventive compounds of formula (I) also show in vivo antitumor activity in solid tumor bearing mice.

The present invention also provides a method for preparing a compound of formula (I) according to the invention. On all the schemes, unless specified otherwise, $R^1$, $R^2$, X and Ar are as described above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel and/or by recrystallization.

The method for preparing a compound of formula (I) according to the invention comprises the following successive steps:
a) condensing formaldehyde, 1,3-cyclohexanedione or 1,3-cyclopentanedione, and an aniline (II):

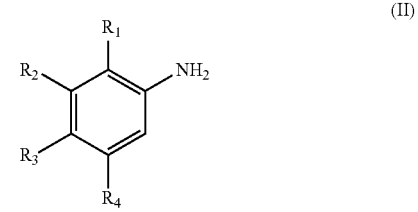

(II)

followed by oxidation, yielding an intermediate (III):

b) oxidizing intermediate (III) so as to obtain an N-oxide (IV):

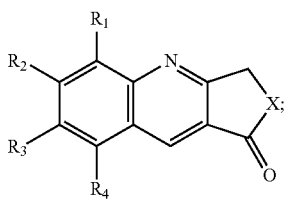
(III)

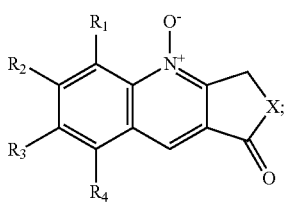
(IV)

c) reacting N-oxide (IV) with a chlorinating agent, yielding intermediate (V):

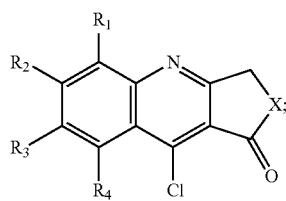
(V)

d) reacting intermediate (V) with an aniline $ArNH_2$ (VI) so as to obtain a compound of formula (I);
e) optionally treating the obtained compound of formula (I) with an acid so as to obtain a salt of said compound of formula (I)

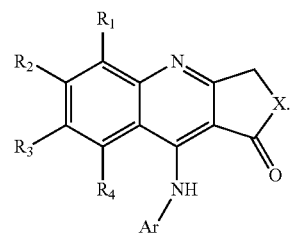
(I)

Advantageously, the three-component reaction (condensing of formaldehyde, 1,3-cyclohexanedione or 1,3-cyclopentanedione, and aniline (II)) substep of a) is a one-pot reaction.

The condensing substep of step a) may advantageously be carried out in refluxing ethanol.

The oxidizing agent in the oxidation substep of a) is manganese dioxide, dimethyl sulfoxide, 2,3-dichloro-5,6-dicyano-1,4-quinone, more preferably it is manganese dioxide Preferably, the oxidizing agent in step b) is an acetic acid-hydrogen peroxide mixture or m-chloroperbenzoic acid, more preferably it is m-chloroperbenzoic acid.

Advantageously, the chlorinating agent in step c) is phosphorus pentachloride, phosphorus oxytrichloride or thionyl chloride, more preferably it is phosphorus oxytrichloride.

Advantageously, the aniline (II) in step a) is 3,4-dimethoxyaniline, 3,4-dimethylaniline or 6-amino-1,4-benzodioxan, more preferably it is 5-amino-1,3-benzodioxole.

Advantageously, the aniline (VI) in step d) is 3,4,5-trimethoxyaniline, 3,4-dimethoxyaniline, 3,4-methylenedioxyaniline, 3,5-dimethoxyaniline, 3-methoxy- or 4-hydroxy-3-methoxyaniline, more preferably it is 3,4,5-trimethoxyaniline.

The following examples are meant to illustrate the present invention, but do not intend to limit its scope in any way. The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

EXAMPLES

Example 1: Synthesis of 6,7-(methylenedioxy)-9-[(3,4,5-trimethoxyphenyl)amino]-3,4-dihydroacridin-1(2H)-one hydrochloride (SGR307.HCl)

Synthesis of SGR307•HCl

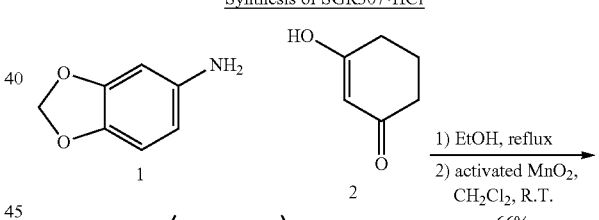

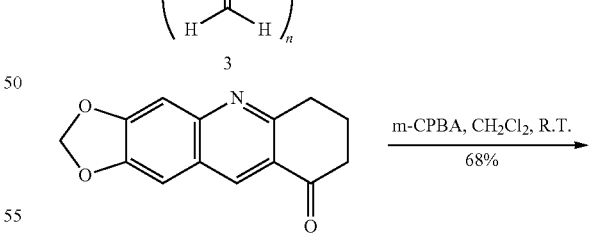

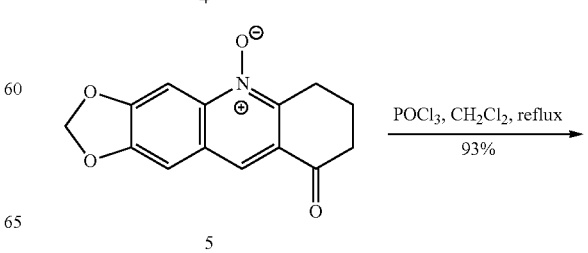

15

-continued

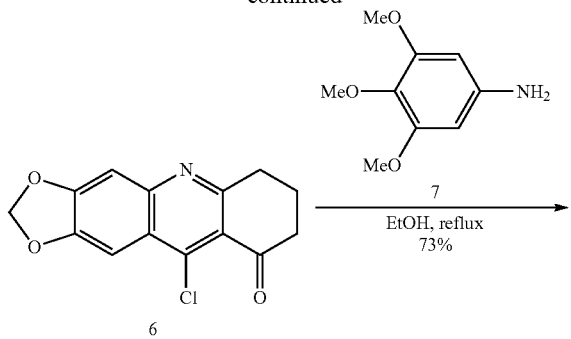

Step 1:

6,7-(Methylenedioxy)-3,4-dihydroacridin-1(2H)-one (4)

An equimolecular (45 mmol) mixture of 3,4-(methylenedioxy)aniline 1 (6.17 g), paraformaldehyde 3 (1.35 g), and cyclohexane-1,3-dione 2 (5.04 g) in EtOH (220 mL) was refluxed for 1.5 h. Half of the solvent was eliminated under reduced pressure and the resulting solid was filtered off. To a solution of this mixture of dihydro and aromatic compounds (7.56 g) in dichloromethane (1.60 L), was added activated $MnO_2$ (85% of purity) (6.74 g). After stirring at room temperature for 1.5 hour, the reaction mixture was filtered through a pad of Celite and the solvent was removed to afford analytically pure 4 as a white powder (7.22 g, 66%). mp: 210° C.; $^1$H NMR (300 MHz, DMSO-$d_6$): δ=2.12 (q, J=6 Hz, 2H, 3-H), 2.69 (t, J=6 Hz, 2H, 2-H), 3.13 (t, J=6 Hz, 2H, 4-H), 6.25 (s, 2H, O—$CH_2$—O), 7.33 (s, 1H, 5-H), 7.50 (s, 1H, 8-H), 8.63 (s, 1H, 9-H).

Step 2

6,7-(Methylenedioxy)-10-oxy-3,4-dihydroacridin-1(2H)-one (5)

To a solution of acridine 4 (1.91 g, 7.9 mmol) in dichloromethane (100 mL) was added m-chloroperbenzoic acid (70% of purity) (3.91 g, 15.8 mmol). After 72 h of stirring at room temperature, a 1M solution of sodium hydroxide (160 mL) was added and the reaction mixture was vigorously stirred for 10 minutes. The water layer was then extracted by dichloromethane (2×50 mL). The combined organic phases were washed with water until a neutral pH was reached, dried over $Na_2SO_4$, filtered and then the solvent was eliminated under reduced pressure to give 5 as a yellow powder (1.40 g, 68%) which was used without other purification in the next step. A sample was purified by flash chromatography on silica gel (dichloromethane/methanol 95/5) for elemental analysis. mp: 262° C.; $^1$H NMR (300 MHz, DMSO-$d_6$): δ=2.13 (q, J=6.2 Hz, 2H, 3-H), 2.67 (t, J=6.2 Hz, 2H, 2-H), 3.18 (t, J=6.2 Hz, 2H, 4-H), 6.31 (s, 2H, O—$CH_2$—O), 7.63 (s, 1H, 8-H), 7.86 (s, 1H, 5-H), 8.23 (s, 1H, 9-H).

Step 3

9-Chloro-6,7-(methylenedioxy)-3,4-dihydroacridin-1(2H)-one (6)

To a solution of acridine N-oxide 5 (1.36 g, 5.2 mmol) in dichloromethane (250 mL) was added $POCl_3$ (5.9 mL, 63.6 mmol). After refluxing for 48 h, were added water (100 mL) and then a saturated aqueous solution of $NaHCO_3$ until a pH of 8 was reached. After extraction of the aqueous layer with dichloromethane (2×100 mL), the organic phases were washed with water, dried over $Na_2SO_4$, filtered and then the solvent was eliminated under reduced pressure to give 6 as a light brown powder (1.33 g, 93%) which was used without other purification in the next step. A sample was purified by flash chromatography on silica gel (dichloromethane). Mp: 214° C.; $^1$H NMR (300 MHz, DMSO-$d_6$): δ=2.21 (q, J=6.4 Hz, 2H, 3-H), 2.81 (t, J=6.4 Hz, 2H, 2-H), 3.25 (t, J=6.4 Hz, 2H, 4-H), 6.19 (s, 2H, O—$CH_2$—O), 7.29 (s, 1H, 5-H), 7.70 (s, 1H, 8-H).

Step 4

6,7-(Methylenedioxy)-9-(3,4,5-trimethoxyphenylamino)-3,4-dihydroacridin-1(2H)-one, hydrochloride (SGR 307.HCl)

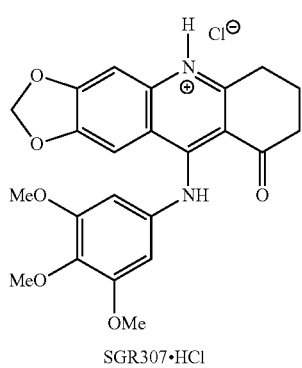

A mixture of chloroacridine 6 (698 mg, 2.53 mmol) and 3,4,5-trimethoxyaniline (7) (510 mg, 2.78 mmol) in EtOH (350 mL) was refluxed for 5 h. The solvent was evaporated under reduced pressure, the resulting precipitate was filtered off, and then recrystallized from EtOH to give SGR 307.HCl as a pale yellow powder (848 mg, 73%). mp: 244-246° C.; $^1$H NMR (300 MHz, DMSO-$d_6$): δ=2.16 (q, J=6.1 Hz, 2H, 3-H), 2.79 (t, J=6.1 Hz, 2H, 2-H), 3.30 (t, J=6.1 Hz, 2H, 4-H), 3.70 (s, 3H, 4'-OMe), 3.72 (s, 6H, 2× OMe), 6.26 (s, 2H, O—$CH_2$—O), 6.72 (s, 1H, 8-H), 6.75 (s, 2H, 2'-H et 6'-H), 7.56 (s, 1H, 5-H), 12.73 (s, 1H, NH), 15.15 (s, 1H, 10-H); HRMS (ES$^+$): m/z calculated for $C_{23}H_{23}N_2O_6$ [M$^+$]: 423.1556, found: 423,1508.

Other analogs have been prepared using the similar protocols, varying the starting materials. The pKa for protonation of these compounds has also been calculated, using SPARC software http://archemcalc./sparc/:

| Name | Formula | Characterization | Calculated pKa for protonation |
|---|---|---|---|
| 6,7-(Methylenedioxy)-9-(3,4,5-trimethoxyphenylamino)-3,4-dihydroacridin-1(2H)-one, hydrochloride (SGR 307•HCl) | 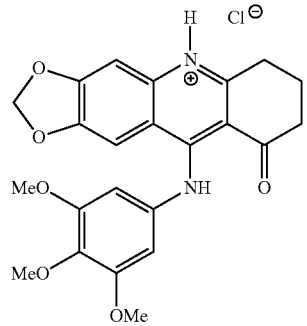 | See above | 8.4 |
| 6,7-(Methylenedioxy)-9-(3,4-methylenedioxyphenyl-amino)-3,4-dihydroacridin-1(2H)-one, hydrochloride (SGR 355•HCl) | 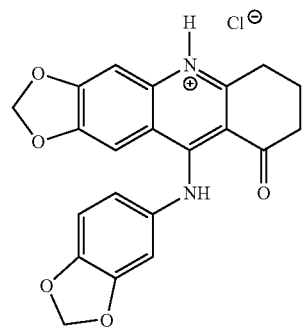 [SMILES: O=C1CCCc2[nH+]c3cc4c(cc3c(Nc3ccc5c(c3)OCO5)c21)OCO4 ; [Cl-]] | Mp: 260° C.; $^1$H NMR (300 MHz, DMSO-$d_6$): δ = 2.16 (q, J = 6.1 Hz, 2H, 3-H), 2.79 (t, J = 6.1 Hz, 2H, 2-H), 3.31 (t, J = 6.1 Hz, 2H, 4-H), 6.14 (s, 2H, O—CH$_2$—O), 6.26 (s, 2H, O—CH$_2$—O), 6.73 (s, 1H, 5-H or 8-H), 6.86 (dd, J = 1.7 and J = 8.2 Hz, 1H, 6'-H), 7.04 (m, 2H, 5'-H and 2'-H), 7.56 (s, 1H, 5-H or 8-H), 12.73 (s, 1H, NH), 15.01 (s, 1H, 10-H); Anal. Calcd. for: $C_{21}H_{17}ClN_2O_5 \cdot C_2H_5OH \cdot 0.5 H_2O$: C, 59.04; H, 5.17; N, 5.99, found: C, 59.16; H, 5.14; N, 5.93. | 8.4 |
| 6,7-(Methylenedioxy)-9-(3-methoxyphenylamino)-3,4-dihydroacridin-1(2H)-one, hydrochloride (SGR 356•HCl) | 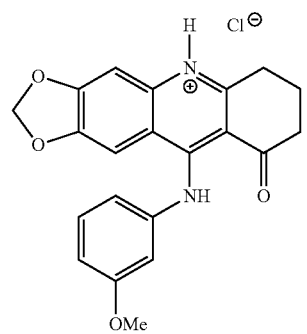 [SMILES: COc1cccc(Nc2c3c([nH+]c4cc5c(cc24)OCO5)CCCC3=O)c1 ; [Cl-]] | Mp: 258° C.; $^1$H NMR (300 MHz, DMSO-$d_6$): δ = 2.17 (q, J = 6.1 Hz, 2H, 3-H), 2.79 (t, J = 6.1 Hz, 2H, 2-H), 3.32 (t, J = 6.1 Hz, 2H, 4-H), 3.77 (s, 3H, OMe), 6.25 (s, 2H, O—CH$_2$—O), 6.70 (s, 1H, 5-H or 8-H), 6.89 (d, J = 7.7 Hz, 1H, 4'H or 6'-H), 6.99 (m, 2H, 2'-H and 4'H or 6'-H), 7.40 (t, J = 7.7 Hz, 1H, 5'H), 7.59 (s, 1H, 5-H or 8-H), 12.71 (s, 1H, NH), 15.20 (s, 1H, 10-H); Anal. Calcd. for: $C_{21}H_{19}ClN_2O_4 \cdot 0.25 C_2H_5OH \cdot 0.25 H_2O$: C, 62.24; H, 5.10; N, 6.75. Found: C, 62.29; H, 4.99; N, 6.79. | 8.16 |
| 6,7-(Methylenedioxy)-9-(3,5-dimethoxyphenylamino)-3,4-dihydroacridin-1(2H)-one, hydrochloride (SGR 363•HCl) | 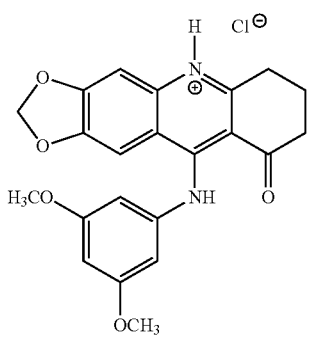 [SMILES: COc1cc(Nc2c3c([nH+]c4cc5c(cc24)OCO5)CCCC3=O)cc(OC)c1 ; [Cl-]] | Mp: 256° C.; $^1$H NMR (300 MHz, DMSO-$d_6$): δ = 2.16 (q, J = 6.1 Hz, 2H, 3-H), 2.78 (t, J = 6.1 Hz, 2H, 2-H), 3.30 (t, J = 6.1 Hz, 2H, 4-H), 3.74 (s, 6H, 2 × OMe), 6.27 (s, 2H, O—CH$_2$—O), 6.55 (s, 3H, 2'-H, 4'H, 6'-H), 6.80 (s, 1H, 5-H or 8-H), 7.58 (s, 1H, 5-H or 8-H), 12.63 (s, 1H, NH), 15.07 (s, 1H, 10-H); Anal. Calcd. for: $C_{22}H_{21}ClN_2O_5 \cdot 0.25 H_2O$: C, 60.97; H, 5.00; N, 6.46. Found: C, 61.02; H, 5.01; N, 6.33. | 8.29 |

| Name | Formula | Characterization | Calculated pKa for protonation |
|---|---|---|---|
| 6,7-(Methylenedioxy)-9-(3,4,5-trimethoxyphenylamino)-2,3-dihydro-1H-cyclopenta[b]quinolin-1-one, hydrochloride (SGR 358•HCl) | | Mp: 267° C.; ¹H NMR (300 MHz, DMSO-d$_6$): δ = 2.79 (m, 2H, 2-H), 3.32 (m, 2H, 3-H), 3.71 (s, 3H, OMe), 3.73 (s, 6H, 2 × OMe), 6.30 (s, 2H, O—CH$_2$—O), 6.76 (s, 2H, 2'-H and 6'-H), 7.12 (s, 1H, 5-H or 8-H), 7.50 (s, 1H, 5-H or 8-H), 10.71 (s, 1H, NH), 15.37 (s, 1H, 10-H); Anal. Calcd. for: C$_{22}$H$_{21}$ClN$_2$O$_6$•0.25 C$_2$H$_5$OH•1.25 H$_2$O: C, 56.43; H, 5.26; N, 5.85. Found: C, 56.41; H, 5.04; N, 5.74. Calcd. for: C$_{22}$H$_{21}$ClN$_2$O$_6$•H$_2$O: C, 57.08; H, 5.01; N, 6.05. Found: C, 57.21; H, 5.04; N, 5.99. | 8.28 |
| 6,7-(Methylenedioxy)-9-(3,4-dimethoxyphenylamino)-2,3-dihydro-1H-cyclopenta[b]quinolin-1-one, hydrochloride (SGR 359•HCl) | | Mp: 256° C.; ¹H NMR (300 MHz, DMSO-d$_6$): δ = 2.81 (m, 2H, 2-H), 3.31 (m, 2H, 3-H), 3.73 (s, 3H, OMe), 3.82 (s, 3H, OMe), 6.24 (s, 2H, O—CH$_2$—O), 6.86 (s, 1H, 5-H or 8-H), 6.93 (dd, J = 2.1 and J = 8.6 Hz, 1H, 6'-H), 7.05 (d, J = 8.6 Hz, 1H, 5'-H), 7.07 (d, J = 2.1 Hz, 1H, 2'-H), 7.50 (s, 1H, 5-H or 8-H), 10.75 (s, 1H, NH), 15.34 (s, 1H, 10-H); Anal. Calcd. for: C$_{21}$H$_{19}$ClN$_2$O$_5$•1.25 H$_2$O: C, 57.67; H, 4.96; N, 6.41. Found: C, 57.63; H, 4.89; N, 6.10. | 8.24 |
| 6,7-(Ethylenedioxy)-9-(3,4,5-trimethoxyphenylamino)-3,4-dihydroacridin-1(2H)-one, hydrochloride (SGR 360•HCl) | | Mp: 266° C.; ¹H NMR (300 MHz, DMSO-d$_6$): δ = 2.16 (q, J = 6.1 Hz, 2H, 3-H), 2.80 (t, J = 6.1 Hz, 2H, 2-H), 3.31 (t, J = 6.1 Hz, 2H, 4-H), 3.72 (s, 9H, 3 × OMe), 4.28 (m, 2H, OCH$_2$), 4.42 (m, 2H, OCH$_2$), 6.79 (s, 2H, 2'-H, 6'-H), 6.87 (s, 1H, 5-H or 8-H), 7.53 (s, 1H, 5-H or 8-H), 13.06 (s, 1H, NH), 14.83 (s, 1H, 10-H); Anal. Calcd. for: C$_{24}$H$_{25}$ClN$_2$O$_6$: C, 60.95; H, 5.33; N, 5.92. Found: C, 60.83; H, 5.42; N, 5.96. | 8.37 |
| 6,7-(Ethylenedioxy)-9-(3,5-dimethoxyphenylamino)-3,4-dihydroacridin-1(2H)-one, hydrochloride (SGR 361•HCl) | | Mp: 254-255° C.; ¹H NMR (300 MHz, DMSO-d$_6$): δ = 2.16 (q, J = 7.8 Hz, 2H, 3-H), 2.79 (t, J = 7.8 Hz, 2H, 2-H), 3.32 (t, J = 7.8 Hz, 2H, 4-H), 3.74 (s, 6H, 2 × OMe), 4.29 (m, 2H, O—CH$_2$—), 4.43 (m, 2H, O—CH$_2$—), 6.60 (s, 3H, 2'-H, 4'H, 6'-H), 6.94 (s, 1H, 5-H or 8-H), 7.61 (s, 1H, 5-H or 8-H), 12.99 (s, 1H, NH), 15.17 (s, 1H, 10-H); Anal. Calcd. for: C$_{23}$H$_{23}$ClN$_2$O$_5$•0.75 H$_2$O: C, 60.53; H, 5.41; N, 6.14. Found: C, 60.30; H, 5.33; N: 5.99. | 8.27 |

| Name | Formula | Characterization | Calculated pKa for protonation |
|---|---|---|---|
| 6,7-(Dimethyl)-9-(3,4,5-trimethoxyphenylamino)-3,4-dihydroacridin-1(2H)-one, hydrochloride (SGR 364•HCl) | | Mp: 216° C.; $^1$H NMR (300 MHz, DMSO-d$_6$): δ = 2.07 (s, 3H, 6-Me or 7-Me), 2.18 (q, J = 6.1 Hz, 2H, 3-H), 2.40 (s, 3H, 6-Me or 7-Me), 2.81 (t, J = 6.1 Hz, 2H, 2-H), 3.37 (t, J = 6.1 Hz, 2H, 4-H), 3.71 (s, 3H, 4'-OMe), 3.73 (s, 6H, 2 × OMe), 6.82 (s, 2H, 2'-H, 6'-H), 7.21 (s, 1H, 5-H or 8-H), 7.88 (s, 1H, 5-H or 8-H), 13.15 (s, 1H, NH), 15.09 (s, 1H, 10-H); Anal. Calcd. for: $C_{24}H_{27}ClN_2O_4$•0.25 $H_2O$: C, 64.42; H, 6.20; N, 6.26. Found: C, 64.12; H, 6.29; N, 5.99. | 7.61 |

Example 2: In Vitro and In Vivo Antitumor Activity of SGR307.HCl

Materials and Methods for the Biological Evaluations
Endothelial Cell Morphology Evaluation To assess the effects of the compounds on the morphology of endothelial cells, the EAhy 926 endothelial cell line was used, which is derived from the fusion of human umbilical vein endothelial cells (HUVEC) with the permanent human cell line A549 (Edgell et al, Proc. Natl. Acad. Sci. U.S.A., 1983, vol 80, issue 12, 3734-3737). The EAhy 926 cell line is considered as a good representative of native HUVEC because it expresses most of the biochemical markers of parental HUVEC (Bouis et al., Angiogenesis., 2001, 4, 91-102). EAhy 926 cells were grown in DMEM containing 2 mM L-glutamine, 10% foetal bovine serum, 100 U/mL penicillin and 100 μg/mL streptomycin in a humidified atmosphere (37° C., 5% $CO_2$). Exponentially growing EAhy 926 cells were plated onto 96 well plates at 5000 cells/100 μL/well. Twenty-four hours after plating, the medium was aspirated, and 100 μL of medium containing the test compound was added to the well containing the cells (in triplicate) and incubated for 2 h (37° C., 5% $CO_2$). The highest concentration used was 100 μM followed by serial two-fold dilutions down to low nanomolar concentrations, if needed for the most morphologically active compounds. After the 2 h-incubation period, digital photographs were taken of representative centre areas of each well at a magnification of 100× and 200×. The results are presented as the minimum concentration that could elicit the rounding up of more than 15% of cells in a field in order to exclude normal mitotic cells which is less that 15% in control 1% DMSO treated cells. Triplicate concentrations on the same plate were routinely carried out. CA4 was included in the experiments as a positive internal standard.

Endothelial Cell Cords Disruption Assay

Eahy 926 endothelial cells were seeded onto a Matrigel layer in 6 well plates and allowed to form microvascular structures for 48 h (cords). The cords were exposed for 2 hours to various concentrations of SGR307.HCl from 0.005 to 100 μM and to combretastatin A4 (CA4) at 1 μM. In this experiment the control solvent used was 1% DMSO final concentration, because this solvent was required to solubilize combretastatin A4 used as a positive internal control. Digital photographs of the same plate region were taken before drug application and two hours after.

Tubulin Polymerization Inhibition Assay

Tubulin assembly in microtubules was carried out using the fluorescent dye DAPI (4',6-diamidino-2-phenylindole) (Bonne et al., J. Biol. Chem., 1985, 260, 2819-2825) in a 96-well plate format as described (Bane et al in Zhou, J. (Ed.), Microtubule Protocols. Humana Press, Totowa, N.J., 2007, 281-288; Barron et al., Anal. Biochem., 2003, 315, 49-56). The standard assay was performed as follows: wells were charged with tubulin (Cytoskeleton, 97% pure, final concentration 1 mg/ml) in PME buffer (100 mM PIPES (1,4-piperazinebis(ethanesulfonic acid); 1 mM $MgSO_4$; 2 mM EGTA) with 10 μM DAPI and varying concentrations of the test compounds using colchicine at 30 μM as a positive internal standard control. The final concentrations used for the test compounds were started at 30 μM and diluted in 3-fold decrements until no inhibition was observed. Triplicate wells were run for each concentration. After pre-incubation at room temperature for 45 min, 1 mM GTP (5 μL) was added to each well to initiate tubulin polymerization, and the plate was then transferred to a thermostated Victor plate reader at 37° C. for an additional 2 h. Fluorescence was then read at the excitation wavelength of 360 nm and emission of 450 nm. The percent inhibition was determined as follows: 1−(ΔF(sample/ΔF(control)×100, where ΔF control=F(no inhibition)−F(complete inhibition), and ΔF sample=F(sample)−F(complete inhibition with colchicine). The $IC_{50}$ for compound-induced inhibition of tubulin polymerization is the concentration at which the extent of inhibition of polymerization is 50% of the maximum value, as determined from the semi-logarithmic plot of percent inhibition as a function of the logarithm of drug concentration fitted to a sigmoidal model with variable slope using the nonlinear regression program SigmaPlot (Jandel Scientific). In these conditions the $IC_{50}$ value for colchicine inhibition of tubulin polymerization was 0.36 μM.

Cytotoxicity Assay for Murine Cancer Cells

Murine B16 melanoma cells, Lewis lung carcinoma cells and colon 26 carcinoma cells were grown in DMEM medium containing 2 mM L-glutamine, 10% foetal bovine serum, 100 U/mL penicillin and 100 μg/mL streptomycin (37° C., 5% $CO_2$). SGR307.HCl and other compounds of the invention were dissolved in water at a stock concentration of 2.5 mg/mL and were further diluted in cell culture medium. Exponentially growing cells were plated onto 96-well plates at 5000 cells per well in 100 μL of culture medium. 24 h after plating, 100 μl of medium containing the tested compound at final concentrations ranging from 0.01 to 100 μM were added to the wells (in triplicate) containing the cells, and incubated for 48 h at 37° C. and 5% $CO_2$. After the 48 h exposure period to the test compounds, cell viability was assayed using the MTT (methylthiazoletetrazolium) test (Scudiero et al., Cancer Res. 1988, 48, 4827-4833) and absorbance was read at 562 nm in a microplate reader (BioKinetics Reader, EL340). Appropriate controls with DMEM only and MTT were run to subtract background absorbance. The concentration of compound that inhibited cell viability by 50% (inhibitory concentration for 50% of cells, or $IC_{50}$) was determined using the GraphPad Prism software.

Cytotoxicity Assay for Human Cancer Cells

Human cells were grown in DMEM medium supplemented with 10% fetal calf serum (Invitrogen), in the presence of penicillin, streptomycin and amphotericin B (Fungizone) in 75 $cm^2$ flask under 5% $CO_2$. Cells were plated in 96-well tissue culture microplates at a density of 650 cells/well in 200 μl medium and treated 24 h later with the compound dissolved in DMSO at concentrations ranging from 0.5-10 μM applied using an automated benchstation (Beckman Biomek 3000). Controls received the same volume of DMSO as the test wells (1% final concentration). After a 72 h exposure time, MTS reagent (Promega) was added and incubated for 3 h at 37° C. and the absorbance was read at 490 nm. Results are expressed as the inhibition of cell proliferation calculated as the ratio [(OD490 treated/OD490 control)×100]. For $IC_{50}$ determinations (50% inhibition of cell proliferation) experiments were performed in two independent experiments in duplicate.

Antitumor Activity Evaluation in Tumor-Bearing Mice

Female C57BL/6 and BALB/c mice were purchased from Janvier (Le Genest Saint Isle, France). Mice weighed more than 18 g at the start of treatment and had free access to food and water. Murine tumors were maintained by serial passage in the appropriate mouse strain of origin, i.e., colon tumor 26 (CT26) was passaged in Balb/c mice (Corbett et al., Cancer Res. 1975, 35, 2434-24391975; Corbett et al., Cancer 1977 40, 2660-2680) and Lewis lung carcinoma (Mayo et al, Cancer Chemotherapy Reports Part 2 Supplement, 1972, vol 3, issue 1, 325-330) was maintained in C57BL/6 mice.

The used protocol design, chemotherapy techniques and methods were carried out according to (Corbett et al., Cancer Res, 1982, 42, 1707-1715; Schabel et al., Pharmacology & Therapeutics Part A-Chemotherapy Toxicology and Metabolic Inhibitors, 1977, 1, 411-435). Briefly, tumors were implanted subcutaneously (s.c.) and bilaterally on day 1. Animals were randomly assigned to treatment (T) or control (C) groups. Tumors were measured using a caliper two to five times weekly (according to tumor growth rate) until the tumor reached 2500 $mm^3$. Tumor volumes were estimated from two-dimensional measurements using the following formula: tumor volume ($mm^3$)=[length (mm)×$width^2(mm^2)$]/2. Mice body weights were recorded two to three times weekly. The day of death was recorded, and thoracic and abdominal cavities were examined macroscopically to assess probable cause of death.

SGR307.HCl Preparation for In Vivo Administration

SGR307.HCl was prepared by dilution in sterile water, normal saline or 0.5% dextrose and administered intraperitoneally (i.p.) in a volume of 200 μl. Drug doses were adjusted based on body weight at start of treatment. A dose-response evaluation was performed in each trial to determine the highest non-toxic dose (HNTD), defined as the highest drug dose inducing less than 20% body weight loss with no drug-related deaths. Animal body weights included the tumor weights.

End Points Employed for the Evaluation of Antitumor Activity

Tumor Growth Inhibition (T/C Value).

For early stage disease, this is a widely used criterion for the determination of antitumor activity. The tumor volumes were determined the same day for the treated (T) and the control (C) groups. When the median tumor volume of the control group (C) reached the 750 to 1500 $mm^3$ range, the median tumor volume of the treated group (T) was determined, including zeros. The percent T/C value is calculated as follows:

[% T/C=(Median tumor volume of the treated/Median tumor volume of the control)×100]. According to the standards of the American National Cancer Institute, a T/C≤42% is considered the minimum level for activity. A T/C<10% is considered as a high antitumor activity level which justifies further development.

Tumor Growth Delay (T−C Value).

The tumor growth delay is defined as the median difference in days between the treated (T) and the control (C) groups to reach a predetermined tumor volume (750-1000 $mm^3$). Tumor-free survivors are excluded from these calculations and are tabulated separately. This value allows the quantification of the tumor cell kill as defined below.

Tumor Doubling Time (Td).

The Td in days is estimated from the best fit straight line from a log linear tumor growth plot of the control group tumors during the exponential phase (range 100-1000 $mm^3$).

Calculation of the Tumor Log Cell Kill.

For subcutaneous growing tumors, the Log cell kill value was calculated as described by Schabel et al. (Schabel et al., 1977) using the following formula: [(T−C)/3.32]×Td, where the T−C value and Td are the tumor growth delay and the tumor doubling time, respectively, as defined above.

Criteria Used for Antitumor Activity Assessment.

Antitumor activity was assessed using a Log cell kill value ≥0.7, as initially defined by the scientists at the Southern Research Institute (SRI) (Schabel et al., 1977). The following SRI score was used to evaluate antitumor activity based on log cell kill values, as follows: <0.7=− (inactive); 0.7-1.2=+; 1.3-1.9=++; 2.0-2.8=+++; >2.8=++++ (highly active). Complete tumor regression (CR) was defined as tumor regression below the limit of palpation (~62 $mm^3$). Animals without palpable tumors at the end of the study are considered tumor-free survivors (TFS) and were excluded from the T−C value calculation.

Results of In Vitro Biological Evaluations

SGR307.HCl, and Other Compounds of the Invention, Effect on Endothelial Cell Morphology Compounds of the invention were first tested on EAhy 926 endothelial cells, which are transformed HUVEC (human umbilical vein endothelial cells). These cells undergo a rounding up upon a short 2 hour exposure to vascular disrupting agents, e.g. combretastatin A4. FIG. 1 presents a typical rounding up of endothelial cells exposed to SGR307.HCl at the concentration of 1 μM for a short 2 hour exposure time. The significant rounding up of endothelial cells was observed at concentrations as low as 0.06 μM.

SGR307.HCl, Effect on Endothelial Cords

Figure 2:
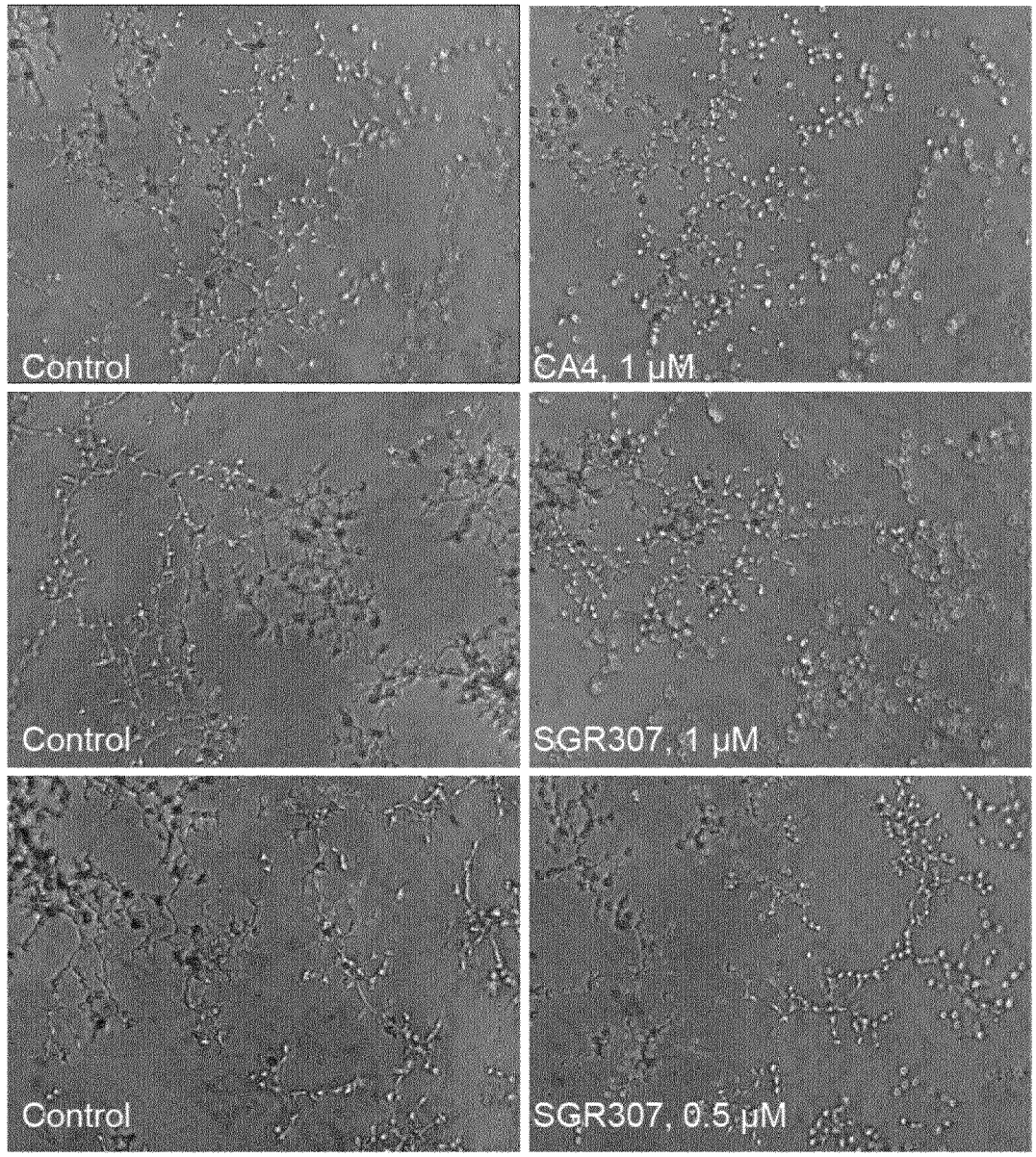
FIG. 2. Destruction of endothelial cell cords by SGR307.HCl. Endothelial preformed cords were exposed for 2 hours to combretastatin A4 (CA4, 1 μM) as an internal control, or to SGR307.HCl at 1 and 0.5 μM. Although SGR307.HCl is water soluble, DMSO was used in this experiment because it was required to solubilize CA4, used as an internal control. The control endothelial cell cords were exposed to 1% DMSO.

Another typical effect of antivascular agents is the disruption of preformed cords of endothelial cells grown on a Matrigel layer. SGR307.HCl effect on preformed endothelial cell cords is presented in FIG. 2. Destruction of endothelial cords by SGR307.HCl can be observed for concentrations as low as 0.5 µM for a 2 hour exposure time. Indeed, SGR307.HCl could destroy endothelial cell cords as effectively as combretastatin A4 at 1 µM, which was included as an internal control.

Figure 3:
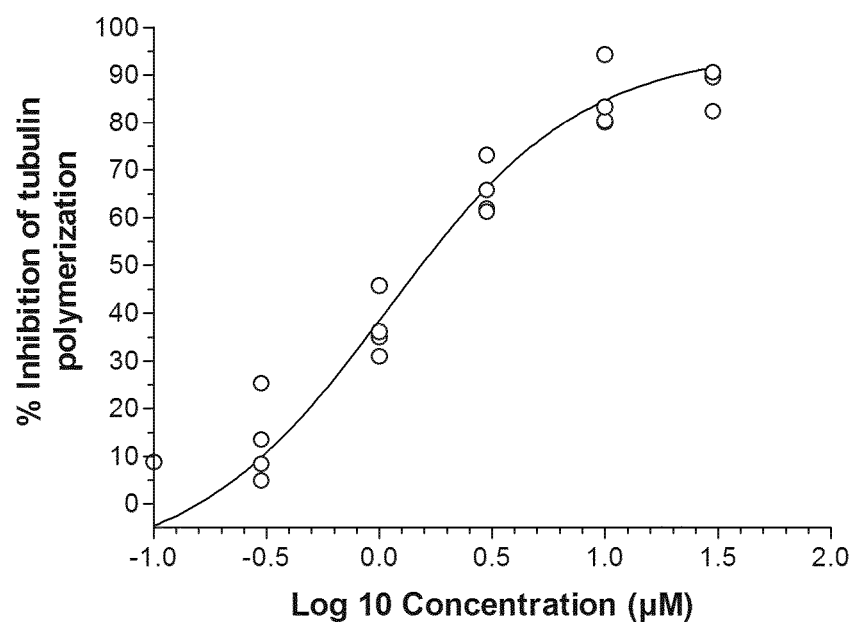
FIG. 3. SGR307.HCl inhibition of tubulin polymerization. The calculated concentration that inhibits 50% of polymerization is 1.09 μM. Tubulin assembly in microtubules was carried out using the fluorescent dye DAPI (4',6-diamidino-2-phenylindole) as described in the Materials and Methods section for the biological evaluations.

SGR307.HCl, and Other Compounds of the Invention, Inhibition of Tubulin Polymerization Because the rounding up of endothelial cells as well as the disruption of endothelial cell cords are both suggestive of a rapid disruption of the cytoskeleton structure, we next tested the effect of compounds of the invention on the tubulin polymerization in vitro. FIG. 3 shows the effect of SGR307.HCl on tubulin polymerization. It can be observed that SGR307.HCl inhibited tubulin polymerization with an IC50 of 1.09 µM. In the same experimental conditions, the standard tubulin polymerization inhibitors podophyllotoxin, colchicine and combretastatin A4 presented IC50s of 0.22, 0.36, and 0.29 µM, respectively.

SGR307.HCl, and Other Compounds of the Invention, Cytotoxicity on Murine Cancer Cells The cytotoxic activity of SGR307.HCl was tested on 3 murine tumor cells, i.e., the B16 melanoma, the Lewis lung carcinoma, and the colon 26 carcinoma. The results presented in Table 1 show the following IC50 values: 4.5, 10.6, and 1.2 µM, for B16, Lewis lung, and colon 26 cells, respectively.

TABLE 1

SGR307.HCl cytotoxicity on murine cancer cells.

| Murine cancer cell line[a] | IC50 value (µM)[b] |
|---|---|
| B16 melanoma | 4.5 |
| Lewis lung carcinoma | 10.6 |
| Colon 26 carcinoma | 1.2 |

[a]Murine cancer cell lines were grown in DMEM as described in Materials and Methods section.
[b]Concentration of SGR307.HCl that produces 50% cell kill in a 48 hour exposure time. Viability was assayed using the MTT reagent.

SGR307.HCl Cytotoxicity on Human Cancer Cells

The cytotoxic activity of SGR307.HCl was further evaluated using a large panel of human cancer cell lines, including most important cancer types, as well as multidrug resistant lines, hormone-sensitive and -resistant line.

Table 2 presents the IC50 of these assays. SGR307.HCl was active at nanomolar concentrations on all cell lines with relatively low IC50 values in the range of 30 to 380 nM.

TABLE 2

SGR307.HCl cytotoxic activity on human cancer cells.[a]

| Human cell line | Origin | IC 50 value (µM) | SEM |
|---|---|---|---|
| U87 | Brain glioblastoma; astrocytoma | 0.126 | 0.017 |
| SF268 | Brain glioma | 0.150 | 0.016 |
| MCF7 | Breast ER+ (hormone dependent) | 0.076 | 0.02 |
| MCF7R | Breast ER+ (Multidrug resistant) | 0.121 | 0.019 |
| MDA231 | Breast ER− (hormone independent) | 0.079 | 0.026 |
| MDA435 | Breast ER− (highly metastatic to lungs) | 0.124 | 0.031 |
| HCT116 | Colorectal carcinoma | 0.068 | 0.016 |
| HCT15 | Colon adenocarcinoma | 0.091 | 0.008 |
| HT29 | Colorectal adenocarcinoma | 0.129 | 0.02 |
| KB | Epidermoid carcinoma | 0.111 | 0.031 |
| A549 | Lung carcinoma | 0.158 | 0.012 |
| MIA PaCa-2 | Pancreatic carcinoma | 0.109 | 0.003 |

TABLE 2-continued

SGR307.HCl cytotoxic activity on human cancer cells.[a]

| Human cell line | Origin | IC 50 value (µM) | SEM |
|---|---|---|---|
| SK-OV3 | Ovarian adenocarcinoma | 0.112 | 0.041 |
| OVCAR8 | Ovarian adenocarcinoma | 0.138 | 0.033 |
| A2780 | Ovarian carcinoma | 0.099 | 0.032 |
| A2780cis | Ovarian carcinoma-cisplatin resistant | 0.109 | 0.013 |
| PC3 | Prostate adenocarcinoma (androgen independent) | 0.098 | 0.017 |
| LnaCap | Prostate adenocarcinoma (androgen dependent) | 0.103 | 0.011 |
| HL60 | Acute promyelocytic leukemia | 0.09 | 0.033 |
| HL60R | Acute promyelocytic leukemia-multidrug resistant | 0.164 | 0.016 |
| K562 | Chronic myelogenous leukemia | 0.083 | 0.003 |
| HepG2 | Hepatocellular carcinoma | 0.139 | 0.026 |
| U937 | Histiocytic lymphoma | 0.121 | 0.007 |
| EPC | Epithelioma (quiescent cell line) | 0.237 | 0.015 |

[a]Cells were exposed for 72 and the number of viable cells was measured using the MTS reagent. $IC_{50}$ values were calculated as the concentration of compound eliciting a 50% inhibition of cell proliferation.

It was noteworthy that all the breast cancer lines were sensitive to SGR307.HCl notwithstanding the fact that they were multidrug resistant or not, or estrogen receptor positive or not. Interestingly, the multidrug resistant cell lines retained sensitivity to SGR307, as shown for the MCF7R and the HL60R cell lines, compared to their sensitive counterpart (MCF7 and HL60).

The colon cell lines, leukemia lines, liver and kidney lines were all quite sensitive to SGR307. Perhaps the only exception is the LnaCap cell line which is an androgen-dependent prostate adenocarcinoma cell line, which was less sensitive to the compound with IC50 of 330-380 nM. However, the androgen-independent PC3 prostate adenocarcinoma was very sensitive to SGR307.HCl (120-130 nM).

Also noteworthy, cisplatin resistant ovarian cell line A2780cis was sensitive to SGR307.

The quiescent cell line EPC was interestingly less sensitive to the compound with IC50 values of 310 and 360 nM.

In conclusion, SGR307.HCl presents a very favorable sensitivity profile with most human cancer cell lines examined.

Results of In Vivo Antitumor Activity

SGR307.HCl Antitumor Activity in Colon 26 Carcinoma Bearing Mice

Figure 4:
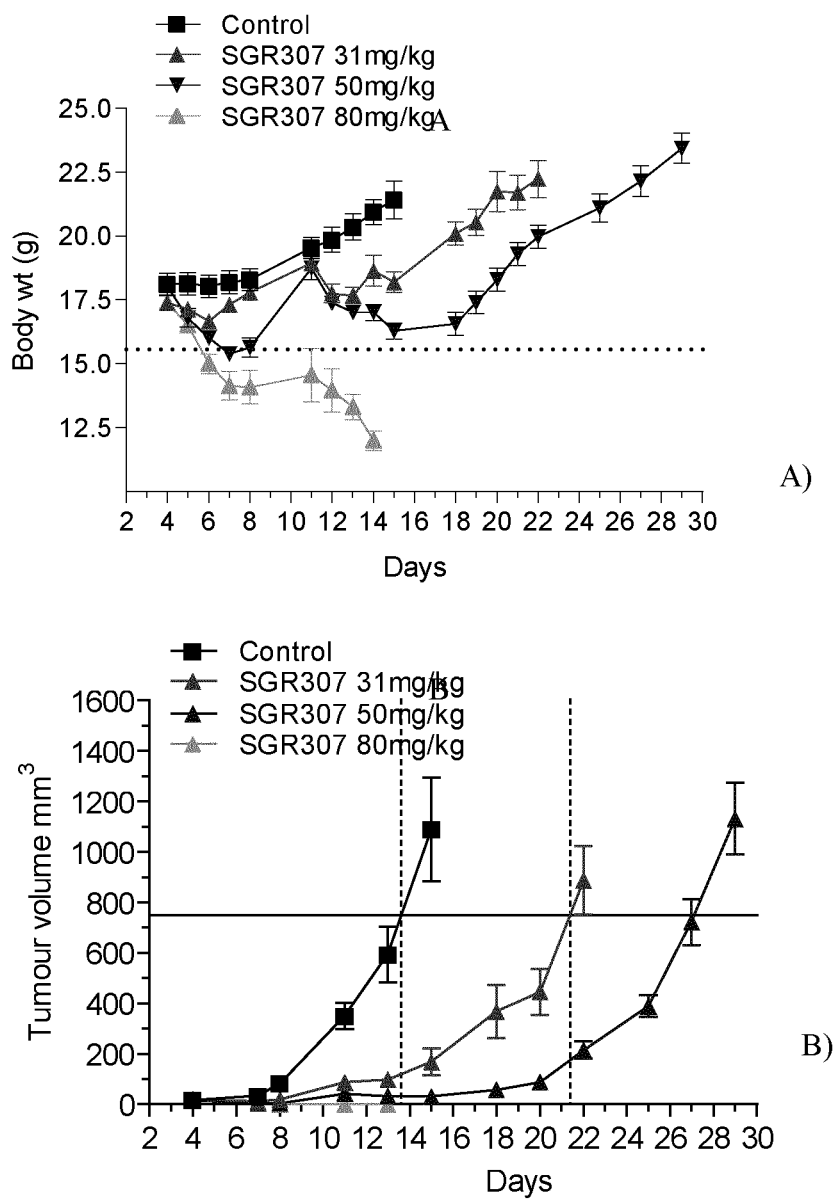
FIG. 4. Toxicity and antitumor effects of SGR307.HCl in colon 26 carcinoma bearing mice. A) Body weight variations at the indicated SGR307.HCl doses injected i.p. on days 4, 5, 11, 12, 14 and 15 post tumor implantation. B) Corresponding antitumoral effect at the indicated doses administered on the same days. Controls received saline solution (0.9% sodium chlorine solution in water).

FIG. 4 presents the antitumor effect of SGR307.HCl in colon 26 bearing mice at drug dosages of 31, 50 and 80 mg/kg injected intraperitoneally (i.p.) on days 4, 5, 11, 12, 14 and 15 post tumor implantation. As can be seen in FIG. 4-A, the 80 mg/kg dose was toxic, causing more than a 20% body weight loss, whereas the 31 and 50 mg/kg were not toxic and afforded a body weight gain during this study.

Anticancer activity was significant at the 31 and 50 mg/kg dose levels, as depicted in FIG. 4-B. A tumor growth delay (T−C) of 7.7 days was observed for the 31 mg/kg dose and of 13.7 days for the 50 mg/kg dose (Table 3). These T−C values indicate a highly active agent according to the criteria used commonly for solid tumor activity (Schabel et al., 1977). In terms of tumor log cell kill values, the 31 mg/kg and the 50 mg/kg doses afforded a 4.6 and a 8.3 value, respectively, which are indicative of a highly active agent.

TABLE 3

SGR307.HCl antitumor activity colon 26 tumor bearing mice.[a]

| IP Agent | Dose mg/kg | Schedule (day) | Total dose mg/kg | Drug death (day of death) | Mean body wt change [g/mouse (day of nadir)] | Mean tumor vol (mm$^3$) day 15 | % T/C day 15 | Time for median tumor to reach 750 mg (day) | T − C (day) | Tumor Log$_{10}$ Cell Kill[b] | Note |
|---|---|---|---|---|---|---|---|---|---|---|---|
| Control | — | 4, 5, 11, 12, 14, 15 | | 0/5 | +3.3 (d15) | 1089 | | 13.5 | — | — | — |
| SGR307 HCl | 31 | 4, 5, 11, 12, 14, 15 | 186 | 0/5 | −0.7 (d6) | 168 | 15.4 | 21.2 | 7.7 | 4.6 | Highly active |
| | 50 | 4, 5, 11, 12, 14, 15 | 300 | 0/5 | −2.6 (d7) | 31 | 2.8 | 27.2 | 13.7 | 8.3 | Highly active |
| | 80.6 | 4, 5, 11, 12, 14, 15 | 484 | 5/5 (7, 8, 11, 2d15) | −5.4 (d14) | | | | | | Toxic |

[a]SGR307.HCl was injected i.p. on the indicated days.
[b]Tumor log$_{10}$ cell kill = [(T − C)/3.32] × Td, where the control tumor doubling time for colon 26 is 2 days.

SGR307.HCl Antitumor Activity in Lewis Lung Carcinoma Bearing Mice

Figure 5:
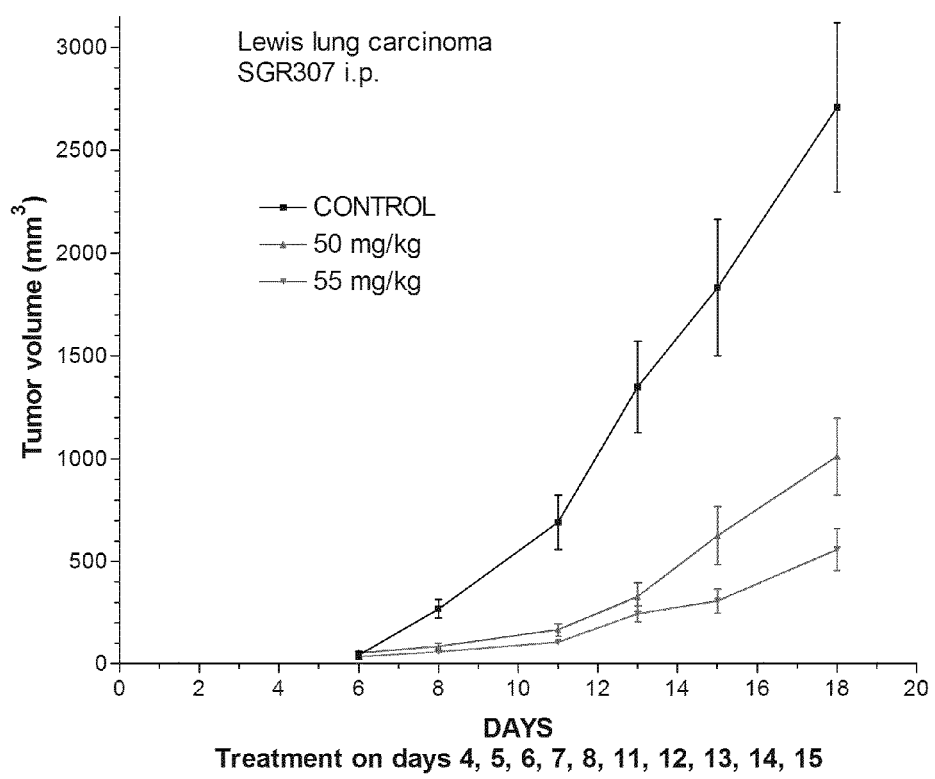
FIG. 5. Antitumor effects of SGR307.HCl in Lewis lung carcinoma bearing mice. SGR307.HCl was injected i.p. on days 4-8 and 11-15 post tumor implantation. Controls received saline solution (0.9% sodium chlorine solution in water).

The antitumor activity was next tested in Lewis lung carcinoma bearing mice. The data depicted in FIG. 5 show an important growth delay for the 50 and the 55 mg/kg doses, when administered i.p. during 5 days per week during two consecutive weeks.

Table 4 show that these doses were not toxic and could elicit a highly significant anticancer effect with tumor growth delays of 4.5 and 5.2 days, for the 50 and the 55 mg/kg dose, respectively. These values correspond to a tumor log$_{10}$ cell kill of 3 and 5.2 for the 50 and 55 mg/kg dose, respectively. This anticancer effect may be qualified as highly active.

TABLE 4

SGR307.HCl antitumor activity in Lewis lung carcinoma bearing mice.[a]

| IP Agent | Dose mg/kg | Schedule (day) | Total dose (mg/kg) | Drug death | Mean body wt change [g/mouse (day of nadir) | Mean tumor volume (mm$^3$) on day 18 (range) | T/C day 18 (%) | Time for median tumor to reach 500 mm$^3$ (day) | T − C (day) | Tumor Log$_{10}$ cell kill[b] | Note |
|---|---|---|---|---|---|---|---|---|---|---|---|
| Control | — | 4, 5, 6, 7, 8, 11, 12, 13, 14, 15 | | 0/5 | +2.4 | 3201 (2136-4495) | | 9.5 | | — | |
| SGR307. HCl | 50 | 4, 5, 6, 7, 8, 11, 12, 13, 14, 15 | 500 | 0/5 | −0.5 (d6) | 1158 (297-2230) | 36.2 | 14.1 | 4.5 | 3.0 | Highly active non toxic |
| | 55 | 4, 5, 6, 7, 8, 11, 12, 13, 14, 15 | 550 | 0/5 | −2.4 (d8) | 619 (457-806) | 19.3 | 17.4 | 7.8 | 5.2 | Highly active Non toxic |

[a]SGR307.HCl was injected i.p. on the indicated days.
[b]Tumor log$_{10}$ cell kill = [(T − C)/3.32] × Td, where the control tumor doubling time for Lewis lung carcinoma is 2.2 days.

Comparative Example 3

The pKA, cytotoxicity on B16 melanoma (cytotoxicity B16) activity, morphological effects (rounding up) on modified HUVEC (EA.hy 926) ($Cm_{arr}$ EA.hy 926), and inhibition of tubulin polymerization (IPT) of compound SGR307.HCl has been compared to those of prior art compounds, and other closely related compounds (see table 5 below). The tests used to evaluate the cytotoxicity on B16 melanoma, the tubulin polymerization as well as the endothelial cell morphology are those described in Example 2.

TABLE 5

Properties and advantages of SGR 307 when compared to prior art compounds

| Name | Formula | Calculated pKa for protonation[1] | Cytotoxicity B16 $IC_{50}$ (µM) | $Cm_{arr}^{2}$ EA.hy 926 (µM) | $IPT^{3}$ IC50 (µM) |
|---|---|---|---|---|---|
| SGR 307•HCl | | 8.4 | 4.5 | 0.06 | 1.09 |
| SGR 357•HCl[4] | | 9.76 | 8.9 | 25 | ND (18% à 30 µM) |
| SGR 356•HCl[4] | | 8.16 | >100 | 50 | ND (35% à 30 µM) |

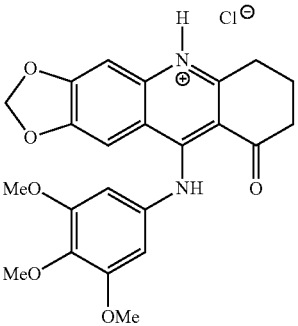 [SMILES: COc1cc(Nc2c3c([nH+]c4cc5c(cc24)OCO5)CCCC3=O)cc(OC)c1OC ; [Cl-]]

TABLE 5-continued

Properties and advantages of SGR 307 when compared to prior art compounds

| Name | Formula | Calculated pKa for protonation[1] | Cytotoxicity B16 IC$_{50}$ (μM) | Cm$_{arr}$[2] EA.hy 926 (μM) | IPT[3] IC50 (μM) |
|---|---|---|---|---|---|
| SGR 230[5] | | 0.81 | 38.4 | 0.12 | 1.04 |
| SGR 231[5] | | 7.1 | 0.40 | 1.95 | 0.42 |
| SGR 308 | | 9.39 | 29.5 | 25 | ND (31% à 30 μM) |
| SGR 309 | | 9.43 | 11 | 3.13 | 18.2 |
| SGR 304 | | 6.41 | >100 | not active at 100 | ND (33% à 30 μM) |

TABLE 5-continued

Properties and advantages of SGR 307 when compared to prior art compounds

| Name | Formula | Calculated pKa for protonation[1] | Cytotoxicity B16 IC$_{50}$ (µM) | Cm$_{arr}$[2] EA.hy 926 (µM) | IPT[3] IC50 (µM) |
|---|---|---|---|---|---|
| SGR 305[6] | | — | >100 | not active at 100 | ND (22% à 30 µM) |
| SGR 306 | | 5.47 | >100 | 12.5 | ND (3% à 30 µM) |

[1]SPARC software http://archemcalc./sparc/
[2]Cm$_{arr}$: Morphological effects (rounding up) on modified HUVEC (EA.hy 926) is expressed as the lowest concentration (µM) at which cell rounding up was observed after a 2 h-incubation period with the test compound.
[3]IPT: Inhibition of tubulin polymerization
[4]comparative compound newly synthetized
[5]Labruère et al. Chem. Med. Chem. 2010, 5, 2016-2025
[6]SGR 305 cannot be protonated on the nitrogen.

Table 6 below presents the properties and advantages of compounds of the invention

TABLE 6

Properties and advantages of compounds of the invention

| Name | Formula | Cytotoxicity B16 IC$_{50}$ (µM) | Cm$_{arr}$[2] EA.hy 926 (µM) | IPT[3] IC50 (µM) |
|---|---|---|---|---|
| SGR 307•HCl | | 4.5 | 0.06 | 1.09 |
| SGR 355•HCl | | 17.4 | 100 | ND (66% à 30 µM) |

TABLE 6-continued

Properties and advantages of compounds of the invention

| Name | Formula | Cytotoxicity B16 IC$_{50}$ (μM) | Cm$_{arr}$[2] EA.hy 926 (μM) | IPT[3] IC50 (μM) |
|---|---|---|---|---|
| SGR 358•HCl | | 1.01 | 0.25 | 5.75 |
| SGR 359•HCl | | 17.4 | 25 | ND (37% à 30 μM) |
| SGR 360•HCl | | 8.1 | 0.06 | 10.5 |
| SGR 363•HCl | | 1.4 | 0.06 | 2.1 |

TABLE 6-continued

Properties and advantages of compounds of the invention

| Name | Formula | Cytotoxicity B16 IC$_{50}$ (μM) | Cm$_{arr}$$^2$ EA.hy 926 (μM) | IPT$^3$ IC50 (μM) |
|---|---|---|---|---|
| SGR 364•HCl | 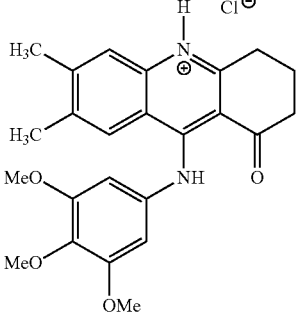 | 12.6 | 6.25 | 24.5 |

Those results show that compounds of the invention have a cytotoxic effect on human cancer cells (IC$_{50}$ B16<20 μM) or a potent antivascular effect (Cm$_{arr}$$^2$ EA.hy 926<1 μM) or preferably both.

It can be deducted from those experiments that some structural features induce unexpected and preferred effects:
- preferably a phenyl substituted with at least two C$_1$-C$_4$-alkoxy on position 3 and 5 as Ar, as it enhances the antivascular activity and the cytotoxicity against tumor cells
- —CH$_2$— or —CH$_2$CH$_2$— and preferably —CH$_2$CH$_2$— as X, as it enhances the antivascular activity of the compounds.
- R$^2$ and R$^3$, are preferably taken together, to form a bridging group —O—CH$_2$—O— or —O—CH$_2$—CH$_2$—O— and more preferably a bridging group —O—CH$_2$—O—, thus enhancing the tubulin inhibiting properties and the cytotoxicity against tumor cells. Furthermore, the bridging groups —O—CH$_2$—O— and —O—CH$_2$—CH$_2$—O— increase the plasma solubility as measured by the calculated pKa for protonation.

CONCLUSIONS

In conclusion, the principal biological properties of SGR307.HCl, a water-soluble compound which is also easy to synthesize, include the followings:
1. it shows an unusual mode of action, namely rounding-up of endothelial cells and destruction of endothelial cords in vitro at nanomolar concentrations;
2. it is a strong tubulin polymerization inhibitor, contrary to the podophyllotoxin analogues used clinically, which are topoisomerase II inhibitors (teniposide or VM26, etoposide or VP16, and Etopophos which is an etoposide prodrug);
3. it is cytotoxic at micromolar concentrations on murine cancer cells;
4. it is highly active in vitro at nanomolar concentrations against several human tumor cell lines;
5. it is active on human multidrug-resistant (MDR) cancer cells;
6. it is active on a cisplatin-resistant human cancer cell line;
7. it shows remarkable in vivo antitumor activity in solid tumor bearing mice including the colon 26 carcinoma and the Lewis lung carcinoma, which are both considered as drug-insensitive tumors.

The invention claimed is:

1. Compound of formula (I):

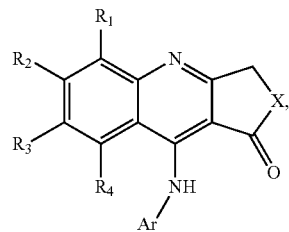

in which

X represents —CH$_2$— or —CH$_2$CH$_2$—;
R$^1$ and R$^4$ are independently selected from the group consisting of H, halogen, C$_1$-C$_4$-alkyl;
R$^2$ and R$^3$ are independently selected from the group consisting of H, OH, C$_1$-C$_4$ alkyl, C$_1$-C$_4$-alkoxy, C1-C4-alkylthio, halogen, trifluoromethyl, CN;
or R$^2$ and R$^3$, taken together, form a bridging group selected from the group consisting of —(CH$_2$)n— and —O—(CH$_2$)m-O—, n being an integer between 3 and 4 and m being 1 or 2;
Ar represents a phenyl or naphthyl group optionally substituted with one to four substituents independently selected from the group consisting of C$_1$-C$_4$-alkyl, OH, C$_1$-C$_4$-alkoxy, C$_1$-C$_4$-alkylthio, halogen, trifluoromethyl, CN,
or a pharmaceutically acceptable salt thereof, and/or a solvate thereof.

2. The compound of claim 1, wherein Ar represents a phenyl or naphthyl group substituted by two substituents independently selected from the group consisting of OH and C$_1$-C$_4$-alkoxy, and optionally substituted with one to two more substituents independently selected from the group consisting of C$_1$-C$_4$-alkyl, OH, C$_1$-C$_4$-alkoxy, C$_1$-C$_4$-alkylthio, halogen, trifluoromethyl, CN.

3. The compound of claim 1, wherein R$^2$ and R$^3$ are independently selected from the group consisting of H, OH, C$_1$-C$_4$ alkyl, C$_1$-C$_4$-alkoxy.

4. The compound of claim 1, wherein R$^2$ and R$^3$, taken together, form the bridging group —O—(CH$_2$)$_m$—O—, m being 1 or 2 and both R$_1$ and R$_4$ represent H.

5. The compound of claim 1, wherein X represents —CH$_2$CH$_2$— and both R$_1$ and R$_4$ represent H.

6. The compound of claim 1, wherein Ar represents a phenyl group substituted with two or three C$_1$-C$_4$-alkoxy groups.

7. The compound of claim 1, wherein Ar is a 3,4,5-trimethoxyphenyl group.

8. The compound of claim 1, wherein said compound of formula (I) is:

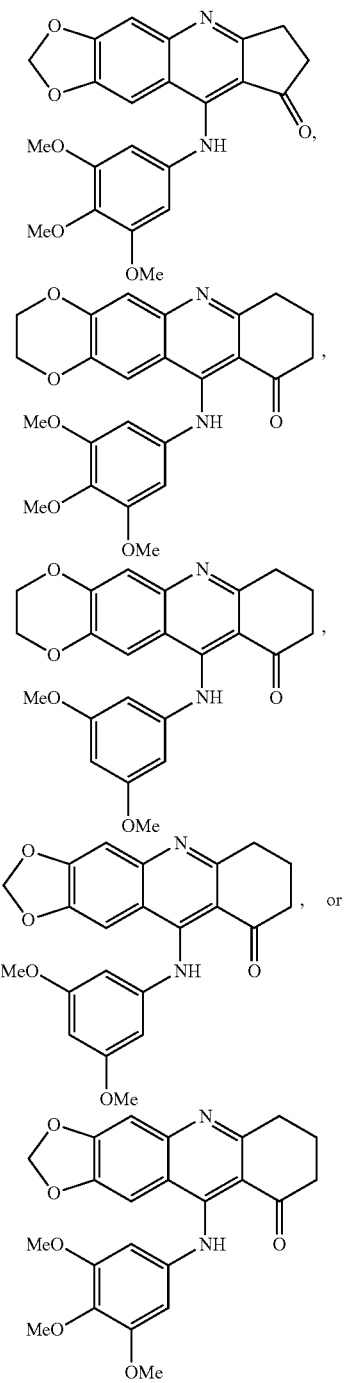

, or or a pharmaceutically acceptable salt thereof and/or solvate thereof.

9. Pharmaceutical composition comprising the compound of claim 1 or a pharmaceutically acceptable salt thereof, and/or a solvate thereof, and a pharmaceutically acceptable excipient.

10. The composition of claim 9, wherein it contains between 0.01% and 10% by weight of said compound of formula (I) or a pharmaceutically acceptable salt thereof and/or solvate thereof, relative to the total weight of the composition.

11. The composition of claim 9, wherein it is formulated as a composition for administration by parenteral or oral route.

12. Kit comprising at least:
    a first composition comprising said compound of formula (I) as defined in claim 1, or a pharmaceutically acceptable salt thereof, optionally in the form of a solvate, and a pharmaceutically acceptable excipient, and
    a second composition comprising another antitumoral agent, selected from cisplatine, methotrexate, cyclophosphamide, doxorubicin, or fluorouracil.

13. A method for treating cancer comprising administering to patient in need thereof the composition of claim 9.

14. The method of claim 13, wherein the cancer is selected from the group consisting of melanoma, lung carcinoma, colon carcinoma, breast cancer, brain tumors, pancreas cancer, leukemia, prostate cancer, lymphoma, and liver cancer.

15. The method of claim 13, wherein the cancer is a multi-drug resistant cancer.

16. The method of claim 13, wherein the composition is used alone or in combination, simultaneously, separately or sequentially, with ionizing or non-ionizing radiations or hyperthermia.

17. Method for preparing a compound of claim 1, comprising the following successive steps:
    a) condensing formaldehyde, 1,3-cyclohexanedione or 1,3-cyclopentanedione and an aniline (II):

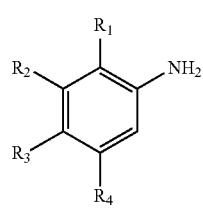

(II)

followed by oxidation, yielding an intermediate (III):

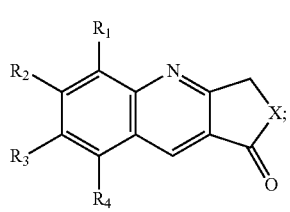

(III)

b) Oxidizing intermediate (III) so as to obtain an N-oxide (IV):

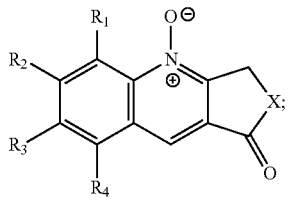

(IV)

c) Reacting N-oxide (IV) with a chlorinating agent, yielding intermediate (V):

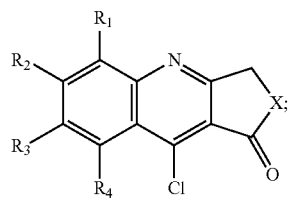

(V)

d) Reacting intermediate (V) with an aniline $ArNH_2$ (VI) so as to obtain a compound of formula (I);

e) optionally treating the obtained compound of formula (I) with an acid so as to obtain a pharmaceutically acceptable salt of said compound of formula (I)

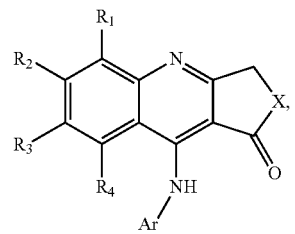

(I)

wherein X, $R_1$, $R_2$, $R_3$, $R_4$ and Ar are as defined in claim 1.

18. A method for treating cancer, comprising administering to a patient in need thereof simultaneously, sequentially or in a staggered manner:
- a first composition comprising said compound of formula (I) as defined in claim 1, or a pharmaceutically acceptable salt thereof, optionally in the form of a solvate, and a pharmaceutically acceptable excipient, and
- a second composition comprising another antitumoral agent, selected from cisplatine, methotrexate, cyclophosphamide, doxorubicin, or fluorouracil.

* * * * *